US012533123B2

(12) United States Patent
Ron et al.

(10) Patent No.: US 12,533,123 B2
(45) Date of Patent: Jan. 27, 2026

(54) METHODS OF USING NEEDLE GUIDE TOOLS FOR PLACING SUTURES IN EYE TISSUE

(71) Applicant: Rambam MedTech Ltd., Haifa (IL)

(72) Inventors: Yonina Ron, Habonim (IL); Roei Sandovsky, Moshav Ein Ayala (IL)

(73) Assignee: RAMBAM MEDTECH LTD., Haifa (IL)

( * ) Notice: Subject to any disclaimer, the term of this patent is extended or adjusted under 35 U.S.C. 154(b) by 175 days.

(21) Appl. No.: 18/565,910

(22) PCT Filed: May 25, 2022

(86) PCT No.: PCT/IL2022/050550
§ 371 (c)(1),
(2) Date: Nov. 30, 2023

(87) PCT Pub. No.: WO2022/254423
PCT Pub. Date: Dec. 8, 2022

(65) Prior Publication Data

US 2025/0040924 A1 Feb. 6, 2025

Related U.S. Application Data

(60) Provisional application No. 63/196,785, filed on Jun. 4, 2021.

(51) Int. Cl.
*A61B 17/06* (2006.01)

(52) U.S. Cl.
CPC .............................. *A61B 17/06066* (2013.01)

(58) Field of Classification Search
CPC .......... A61B 17/06066; A61B 17/0625; A61B 17/06061; A61B 17/0483; A61B 17/062; A61F 9/007

(Continued)

(56) References Cited

U.S. PATENT DOCUMENTS 4,527,564 A 7/1985 Eguchi et al.
5,100,431 A 3/1992 Buster et al.
(Continued)

FOREIGN PATENT DOCUMENTS

CN 204147166 U 2/2015
CN 108294795 A 7/2018
(Continued)

OTHER PUBLICATIONS

Extended European Search Report issued Feb. 20, 2025 in European Application No. 22815492.8.
(Continued)

*Primary Examiner* — Tuan V Nguyen
(74) *Attorney, Agent, or Firm* — Sughrue Mion, PLLC

(57) ABSTRACT

A method is provided for passing a needle and a suture coupled thereto through tissue of a portion of an eye. A needle guide of a needle guide tool is positioned such that a needle-guide surface of the needle guide contacts a body-portion surface of the eye portion, while a proximal needle holder of the needle guide tool holds the needle such that a longitudinal segment of the needle runs alongside the needle-guide surface at a non-zero distance therefrom. The needle-guide surface is distally slid along the body-portion surface such that a distal needle tip penetrates the body-portion surface, passes within the tissue at a depth no more than the non-zero distance, and exits the body-portion surface, while the needle guide and the needle remain outside the eye portion. Thereafter, the needle is released from the proximal needle holder. Other embodiments are also described.

14 Claims, 20 Drawing Sheets

(58) Field of Classification Search
USPC .................................................. 606/139, 144
See application file for complete search history.

(56) References Cited

U.S. PATENT DOCUMENTS

| | | | |
|---|---|---|---|
| 5,391,174 A | 2/1995 | Weston | |
| 5,423,840 A | 6/1995 | Casebeer et al. | |
| 6,143,004 A | 11/2000 | Davis et al. | |
| 6,299,603 B1 | 10/2001 | Hecker et al. | |
| 7,351,205 B2 | 4/2008 | Szczech et al. | |
| 7,993,354 B1 | 8/2011 | Brecher et al. | |
| 9,861,812 B2 | 1/2018 | Gross et al. | |
| 2004/0034372 A1 | 2/2004 | Chu | |
| 2004/0199185 A1 | 10/2004 | Davignon | |
| 2007/0023305 A1* | 2/2007 | Chan .................... | A61B 17/062 206/366 |
| 2008/0269782 A1 | 10/2008 | Stefanchik et al. | |
| 2010/0137831 A1 | 6/2010 | Tsals | |
| 2011/0238038 A1 | 9/2011 | Sefi et al. | |
| 2012/0303046 A1 | 11/2012 | Stone et al. | |
| 2013/0218173 A1 | 8/2013 | Weisel et al. | |
| 2014/0236191 A1 | 8/2014 | Stone et al. | |
| 2015/0351959 A1 | 12/2015 | Clem et al. | |
| 2017/0009389 A1 | 1/2017 | Bach et al. | |
| 2019/0167255 A1 | 6/2019 | Anderson et al. | |
| 2019/0269401 A1 | 9/2019 | Anderson et al. | |
| 2025/0195888 A1* | 6/2025 | Chiapetta ............. | A61N 1/3787 |

FOREIGN PATENT DOCUMENTS

| | | |
|---|---|---|
| GB | 559220 | 2/1944 |
| GB | 2537878 A | 11/2016 |
| JP | 2005-007029 | 1/2005 |
| JP | 2007-117392 | 5/2007 |
| WO | 1998/013092 | 4/1998 |
| WO | 2007/080595 | 7/2007 |
| WO | 2013/010541 | 1/2013 |
| WO | 2018/208294 | 11/2018 |
| WO | 2020/044347 | 3/2020 |

OTHER PUBLICATIONS

An International Search Report and a Written Opinion both dated Jun. 30, 2022, which issued during the prosecution of Applicant's PCT/IL2022/050550.

U.S. Appl. No. 63/196,785, filed Jun. 4, 2021.

* cited by examiner

METHODS OF USING NEEDLE GUIDE TOOLS FOR PLACING SUTURES IN EYE TISSUE

CROSS-REFERENCE TO RELATED APPLICATIONS

The present application is the U.S. national stage of International Application PCT/IL2022/050550, filed May 25, 2022, which published as PCT Publication WO 2022/254423 and which claims priority from U.S. Provisional Application 63/196,785, filed Jun. 4, 2021, which is assigned to the assignee of the present application and incorporated herein by reference.

FIELD OF THE APPLICATION

The present invention relates generally to surgical tools and methods involving the need for specific depth and controlled penetration to a specific tissue, and specifically to surgical tools and methods for insertion of needles during eye surgery.

BACKGROUND OF THE APPLICATION

In certain tissues, such as those found in the eye, it is necessary to transfer a suture at a partial depth to prevent deep, uncontrolled penetration. Deep penetration can cause irreversible damage to the tissue and expose it to infections. For example, the wall of the eyeball consists of the sclera overlying the choroid and the retina. The sclera is on average 0.67 mm thick. The transfer of a needle in the sclera, as done for example in strabismus surgery, must be limited to the partial thickness of the sclera, since full penetration will result in damage to the internal tissues. The current practice involves a handheld needle holder that requires manual needle and suture loading. The depth of penetration while passing the suture in the sclera depends only on the individual surgical skills of each surgeon. An uncontrolled penetration can lead to bleeding, retinal tear, retinal detachment and irreversible damage to vision or even blindness. Moreover, a full thickness suture may create a tract for infectious by allowing elements from the outside into the eyeball, which must remain sterile.

US Patent Application Publication 2004/0199185 to Davignon describes sutures that can be reliably applied to the tissue of sensitive organs in a predetermined and limited depth with minimal surgical skills through the use of a curved suture needle and a suture control apparatus. The suture control apparatus, which can be adjustable, comprises a pair of needle guides that are separated by a space, and a locator surface for engagement with the suture-receiving tissue in the space between the needle guides, with the pair of needle guides and locator surface being preferably carried by a handle. Preferably, the pair of needle guides are curved to provide a radius of curvature substantially equal to the radius of curvature of the curved suture needle. The radius of the curvature of the suture needle and curved needle guides, the distance of the space between the pair of curved needle guides and the location and shape of the locator surface, when pressed against tissue to receive a suture, provide a predetermined and limited depth of penetration of a suture needle and suture, when the curved suture needle is threaded through the pair of curved needle guides and the tissue in the space therebetween.

U.S. Pat. No. 6,299,603 to Hecker et al. describes an invention that relates to an apparatus and method for using the apparatus for injecting an agent into a tissue, particularly into thin tissues such as the sclera of the eye. The invention provides an apparatus and method for effectively imbedding a needle into a tissue at a predetermined penetration approach angle and penetration distance thereby reducing the risk of penetrating the full thickness of the tissue. The invention includes a support element and a needle guide platform disposed on the support element with an external support surface and a channel extending therethrough and terminating in an aperture at the support surface. A needle disposed in the channel is axially movable along an axis of injection through the channel. The needle is movable from a first retracted position to an extended position corresponding to the penetration distance, along the axis of injection. The axis of injection forms a penetration approach angle of up to about 60 degrees with a tangent of the support surface at a point of intersection of the axis of injection with the projection of the support surface across the aperture.

SUMMARY OF THE APPLICATION

Some embodiments of the present invention provide a needle guide tool, which is configured to pass a needle and a suture through tissue of a body portion of a subject, such as an eye, at a desired, stable maximum depth that prevents accidental perforation of adjacent tissue beneath the tissue.

The needle guide tool comprises a needle guide, which is typically supported by a handle, and which is shaped so as to define a needle-guide surface that is configured to slidably contact a body-portion surface of the body portion without penetrating the body-portion surface. The needle guide tool further comprises a proximal needle holder, which is disposed proximal to the needle-guide surface, and which is configured to releasably hold the needle such that a longitudinal segment of the needle runs alongside the needle-guide surface at a non-zero distance therefrom that does not vary along the longitudinal segment of the needle. As a result, the longitudinal segment of the needle is oriented parallel to the needle-guide surface.

During use of the needle guide tool, the needle guide is positioned such that the needle-guide surface contacts a body-portion surface of the body portion, while the proximal needle holder of the needle guide tool holds the needle such that the longitudinal segment of the needle runs alongside the needle-guide surface at the non-zero distance therefrom that does not vary along the longitudinal segment of the needle.

The needle-guide surface is slid distally along the body-portion surface (e.g., sclera of an eye), thereby advancing the needle within the body portion (e.g., a portion of the eye) beneath the body-portion surface at a depth no more than the above-mentioned non-zero distance. More particularly, the needle-guide surface is slid distally along the body-portion surface such that a distal needle tip penetrates the body-portion surface (e.g., sclera of the eye) at a proximal site, passes within the tissue (e.g., sclera) beneath the body-portion surface at the above-mentioned depth, and exits the body-portion surface at a distal site distal to the proximal site, while the needle guide and the needle held by the proximal needle holder remain outside the body portion.

Thereafter, the needle is released from the proximal needle holder, and the needle is distally pulled, so as to (a) pull the suture into the tissue at the proximal site, within the tissue, and out of the tissue at the distal site, and (b) pull the needle out of the tissue at the distal site 78.

Typically, only one hand of the surgeon is required to use the needle guide tool, leaving the other hand free to perform other functions, such as stabilizing the eye.

The needle guide tool thus facilitates the creation of a controlled and uniform partial-thickness suture passage through tissue, which does not depend on the individual skills of each surgeon, and provides a safer and more accurate surgical method.

There is therefore provided, in accordance with an application of the present invention, apparatus including a needle assembly, which includes:

a needle and a suture coupled to the needle; and a needle guide tool, which is configured to pass the needle and the suture through tissue of a body portion of a subject, and which includes:

a needle guide, which is shaped so as to define a needle-guide surface that is configured to slidably contact a body-portion surface of the body portion without penetrating the body-portion surface; and a proximal needle holder, which is disposed proximal to the needle-guide surface, and which releasably holds the needle such that a longitudinal segment of the needle runs alongside the needle-guide surface at a non-zero distance therefrom that does not vary along the longitudinal segment of the needle, such that sliding of the needle-guide surface distally along the body-portion surface advances the needle within the body portion beneath the body-portion surface at a depth no more than the non-zero distance, the depth measured between the body-portion surface and an edge of the needle closest to the body-portion surface.

For some applications, the proximal needle holder releasably holds the needle such that the needle is fixed with respect to the needle guide.

For some applications, the proximal needle holder releasably holds the needle such that the needle is longitudinally fixed with respect to the needle guide.

For some applications, the proximal needle holder includes a proximal needle grasper, which is configured to assume grasping and non-grasping states, and which is in the grasping state, releasably grasping the needle.

For some applications, the proximal needle grasper includes forceps.

For some applications, the needle is straight.

For some applications, the needle is curved.

For some applications, the needle is hollow.

For some applications:

the proximal needle holder releasably holds the needle by directly contacting a longitudinal portion of the needle, without directly contacting any other portions of the needle, and the needle guide tool is configured such that the sliding of the needle-guide surface, while the needle is entirely exposed except along the longitudinal portion of the needle, distally along the body-portion surface advances the needle within the body portion beneath the body-portion surface at the depth no more than the non-zero distance.

There is further provided, in accordance with an application of the present invention, apparatus including a needle guide tool for passing, through tissue of a body portion of a subject, a needle and a suture coupled to the needle, the needle guide tool including:

a needle guide, which is shaped so as to define a needle-guide surface that is configured to slidably contact a body-portion surface of the body portion without penetrating the body-portion surface; and a proximal needle holder, which is disposed proximal to the needle-guide surface, and which is configured to releasably hold the needle such that a longitudinal segment of the needle runs alongside the needle-guide surface at a non-zero distance therefrom that does not vary along the longitudinal segment of the needle, such that sliding of the needle-guide surface along the body-portion surface advances the needle within the tissue beneath the body-portion surface at a depth no more than the non-zero distance, the depth measured between the body-portion surface and an edge of the needle closest to the body-portion surface.

For some applications, the proximal needle holder is configured to releasably hold the needle such that the needle is fixed with respect to the needle guide.

For some applications, the proximal needle holder is configured to releasably hold the needle such that the needle is longitudinally fixed with respect to the needle guide.

For some applications, the proximal needle holder includes a proximal needle grasper, which is configured to assume grasping and non-grasping states, and which is configured, when in the grasping state, to grasp the needle.

For some applications, the proximal needle grasper includes forceps.

For some applications, the needle assembly further including the needle and the suture.

For some applications, the needle is straight.

For some applications, the needle is curved.

For some applications, the needle is hollow.

For some applications:

the proximal needle holder is configured to releasably hold the needle by directly contacting a longitudinal portion of the needle, without directly contacting any other portions of the needle, and the needle guide tool is configured such that the sliding of the needle-guide surface, while the needle is entirely exposed except along the longitudinal portion of the needle, distally along the body-portion surface advances the needle within the body portion beneath the body-portion surface at the depth no more than the non-zero distance.

For some applications, the needle guide tool further includes a handle, which supports the needle guide.

For some applications, the non-zero distance is equal to a value between 0.1 and 1 mm.

For some applications, the needle-guide surface has a length of between 10% and 120% of a length of the needle.

For some applications, the length of the needle-guide surface is between 10% and 50% of the length of the needle.

For some applications, the length of the needle-guide surface is between 40% and 120% of the length of the needle.

For some applications, the needle-guide surface has a length of at least 1.5 mm.

For some applications, the longitudinal segment of the needle has a length of at least 1.5 mm.

For some applications, the longitudinal segment of the needle includes an entirety of the needle that runs alongside the needle-guide surface.

For some applications, the needle-guide surface is straight along a longitudinal axis thereof parallel to the needle when the needle is held by the proximal needle holder.

For some applications, the needle-guide surface is convexly curved along a longitudinal axis thereof parallel to the needle when the needle is held by the proximal needle holder.

For some applications, a lower surface of the needle guide is shaped so as to define (a) the needle-guide surface and (b) a window that passes through the needle guide from an upper surface of the needle guide to the lower surface of the needle guide.

For some applications, a lower surface of the needle guide is shaped so as to define (a) the needle-guide surface and (b) at least one other portion that does not define the needle-guide surface, and the needle does not run alongside the other portion at the non-zero distance from the needle-guide surface.

For some applications, the needle guide, at a distal end portion thereof distal to the needle-guide surface, is shaped so as to define a curved surface that faces partially in a distal direction and partially toward the body-portion surface when the needle-guide surface slidably contacts the body-portion surface.

For some applications, the needle guide tool is not shaped so as to define any passages in which any portion of the needle is disposed when the needle is held by the proximal needle holder.

For some applications, the needle guide tool is not shaped so as to define any passages through which any portions of the needle or the suture pass when the needle is held by the proximal needle holder.

For some applications, the needle guide tool is not shaped so as to define any passages through which any portion of the needle is slidable when the needle is held grasped by the proximal needle holder.

For some applications, the needle guide tool further includes a distal needle holder, which is configured to hold a distal portion of the needle.

For some applications, the distal needle holder is configured to hold the distal portion of the needle such that the longitudinal segment of the needle runs alongside the needle-guide surface at the non-zero distance therefrom that does not vary along the longitudinal segment of the needle, even when the proximal needle holder is not holding the needle.

For some applications, the distal needle holder includes a distal needle grasper, which is configured to assume grasping and non-grasping states, and which is configured, when in the grasping state, to grasp the distal portion of needle.

For some applications, the distal needle grasper includes forceps.

For some applications, the body portion includes a portion of an eye of the subject, and the needle-guide surface is configured to slidably contact the body-portion surface of the eye without penetrating the body-portion surface of the eye.

For some applications, the portion of the eye includes a sclera of the eye, and the needle guide tool is configured such that sliding of the needle-guide surface along the body-portion surface of the portion of the eye, while the proximal needle holder releasably holds the needle, penetrates a distal needle tip through the body-portion surface at a proximal site, passes the distal needle tip within the sclera, and passes the distal needle tip out of the body-portion surface at a distal site distal to the proximal site, while the needle guide and a portion of the needle held by the proximal needle holder remain outside the portion of the eye.

For some applications, the portion of the eye includes a cornea of the eye, and the needle-guide surface is configured to slidably contact the body-portion surface of the cornea without penetrating the body-portion surface of the cornea.

There is still further provided, in accordance with an application of the present invention, apparatus including a needle assembly, which includes:

a needle and a suture coupled to the needle; and a needle guide tool, which is configured to pass the needle and the suture through tissue of a body portion of a subject, and which includes:

- a needle guide, which is shaped so as to define a needle-guide surface that is configured to slidably contact a body-portion surface of the body portion without penetrating the body-portion surface; and
- a proximal needle holder, which is disposed proximal to the needle-guide surface, and which releasably holds the needle such that a longitudinal segment of the needle runs alongside and parallel to the needle-guide surface, such that sliding of the needle-guide surface distally along the body-portion surface advances the needle within the body portion beneath the body-portion surface at a depth no more a distance between the needle-guide surface and the longitudinal segment of the needle, the depth measured between the body-portion surface and an edge of the longitudinal segment of the needle closest to the body-portion surface.

For some applications, the needle guide tool further includes a handle, which supports the needle guide.

For some applications, the longitudinal segment of the needle includes an entirety of the needle that runs alongside the needle-guide surface.

For some applications, the needle is straight, and the needle-guide surface is straight along a longitudinal axis thereof parallel to the needle when the needle is held by the proximal needle holder.

For some applications, the needle is curved, and the needle-guide surface is convexly curved along a longitudinal axis thereof parallel to the needle when the needle is held by the proximal needle holder.

There is additionally provided, in accordance with an application of the present invention, a method for passing, through tissue of a body portion of a subject, a needle and a suture coupled to the needle, the method including:

positioning a needle guide of the needle guide tool such that a needle-guide surface of the needle guide contacts a body-portion surface of the body portion, while a proximal needle holder of the needle guide tool releasably holds the needle such that a longitudinal segment of the needle runs alongside the needle-guide surface at a non-zero distance therefrom that does not vary along the longitudinal segment of the needle;

sliding the needle-guide surface distally along the body-portion surface such that a distal needle tip (a) penetrates the body-portion surface at a proximal site, (b) passes within the tissue beneath the body-portion surface at a depth no more than the non-zero distance, the depth measured between the body-portion surface and an edge of the needle closest to the body-portion surface, and (c) exits the body-portion surface at a distal site distal to the proximal site, while the needle guide and the needle held by the proximal needle holder remain outside the body portion, and while the needle-guide surface slides along the body-portion surface;

thereafter, releasing the needle from the proximal needle holder; and thereafter, distally pulling the needle, so as to (a) pull the suture into the tissue at the proximal site, within the tissue, and out of the tissue at the distal site, and (b) pull the needle out of the tissue at the distal site.

For some applications, positioning a needle guide includes using a handle of the needle guide tool.

For some applications, the non-zero distance is less than a thickness of the tissue within which the distal needle tip passes.

For some applications, the longitudinal segment of the needle includes an entirety of the needle that runs alongside the needle-guide surface.

For some applications, sliding the needle-guide surface along the body-portion surface includes sliding the needle-guide surface along the body-portion surface while the proximal needle holder holds the needle such that the needle is fixed with respect to the needle guide.

For some applications, sliding the needle-guide surface along the body-portion surface includes sliding the needle-guide surface along the body-portion surface while the proximal needle holder holds the needle such that the needle is longitudinally fixed with respect to the needle guide.

For some applications:

the proximal needle holder releasably holds the needle by directly contacting a longitudinal portion of the needle, without directly contacting any other portions of the needle, and sliding the needle-guide surface distally along the body-portion surface includes sliding the needle-guide surface, while the needle is entirely exposed except along the longitudinal portion of the needle, distally along the body-portion surface such that the distal needle tip penetrates the body-portion surface at the proximal site, passes within the tissue beneath the body-portion surface at the depth no more than the non-zero distance, and exits the body-portion surface at the distal site.

For some applications, the needle-guide surface is straight along a longitudinal axis thereof parallel to the needle when the needle is held by the proximal needle holder, and the needle is straight.

For some applications, the needle-guide surface is convexly curved along a longitudinal axis thereof parallel to the needle when the needle is held by the proximal needle holder, and the needle is curved.

For some applications, the needle is hollow.

For some applications:

the proximal needle holder includes a proximal needle grasper, which is configured to assume grasping and non-grasping states, positioning the needle guide includes positioning the needle guide such that the needle-guide surface of the needle guide contacts the body-portion surface while the proximal needle grasper is in the grasping state and holds the needle such that the longitudinal segment of the needle runs alongside the needle-guide surface at the non-zero distance therefrom that does not vary along the longitudinal segment of the needle, and releasing the needle from the proximal needle holder includes releasing the needle from the proximal needle grasper by transitioning the proximal needle grasper to the non-grasping state.

For some applications, the proximal needle grasper includes forceps.

For some applications, the needle guide, at a distal end portion thereof distal to the needle-guide surface, is shaped so as to define a curved surface, and sliding the needle-guide surface along the body-portion surface orients the curved surface facing partially in a distal direction and partially toward the body-portion surface.

For some applications:

the non-zero distance is less than a thickness of the tissue, and sliding the needle-guide surface distally along the body-portion surface includes sliding the needle-guide surface distally along the body-portion surface such that the distal needle tip passes within the tissue beneath the body-portion surface at the depth no more than the non-zero distance without penetrating through the tissue to adjacent tissue beneath the tissue.

For some applications, the non-zero distance is less than 85% of the thickness of the tissue.

For some applications, the method does not include disposing any portions of the needle in any passages defined by the needle guide tool when the needle is held by the proximal needle holder.

For some applications, the method does not include sliding any portions of the needle through any passages defined by the needle guide tool when the needle is held by the proximal needle holder.

For some applications, pulling the needle out of the tissue at the distal site includes:

holding, with a distal needle holder of the needle guide tool, a distal portion of the needle that exited the body-portion surface at the distal site; and while holding the distal portion of the needle with the distal needle holder, sliding the needle-guide surface along the body-portion surface such that the distal needle holder pulls the needle out of the tissue at the distal site.

For some applications, the distal needle holder is configured to hold the distal portion of the needle such that the longitudinal segment of the needle runs alongside the needle-guide surface at the non-zero distance therefrom that does not vary along the longitudinal segment of the needle, even when the proximal needle holder is not holding the needle.

For some applications, the method further includes, before sliding the needle-guide surface along the body-portion surface such that the distal needle holder pulls the needle out of the tissue at the distal site, releasing the needle from the proximal needle holder.

For some applications:

the distal needle holder includes a distal needle grasper, which is configured to assume grasping and non-grasping states, and holding, with the distal needle holder, the distal portion of the needle that exited the body-portion surface at the distal site includes grasping the distal portion of the needle with the distal needle grasper by transitioning the distal needle grasper from the non-grasping state to the grasping state.

For some applications, the distal needle grasper includes forceps.

For some applications, the method does not include passing any portions of the needle or the suture through any passages defined by the needle guide tool when the needle is held by the proximal needle holder.

For some applications, the body portion includes a portion of an eye of the subject, and sliding the needle-guide surface along the body-portion surface includes sliding the needle-guide surface along the body-portion surface of the portion of the eye.

For some applications, the tissue includes a sclera of the eye, and sliding the needle-guide surface along the body-portion surface of the portion of the eye includes sliding the needle-guide surface along the body-portion surface of the portion of the eye such that the distal needle tip penetrates the body-portion surface of the portion of the eye at the proximal site, passes within the sclera of the eye beneath the body-portion surface at the depth no more than the non-zero distance, and exits the body-portion surface of the portion of the eye at the distal site.

For some applications, the tissue includes a cornea of the eye, and sliding the needle-guide surface along the body-portion surface of the portion of the eye includes sliding the needle-guide surface along the body-portion surface of the portion of the eye such that the distal needle tip (a) penetrates the body-portion surface of the portion of the eye at the proximal site, (b) passes within the cornea of the eye beneath the body-portion surface at the depth no more than the non-zero distance, and (c) exits the body-portion surface of the portion of the eye at the distal site.

The present invention will be more fully understood from the following detailed description of embodiments thereof, taken together with the drawings, in which:

DETAILED DESCRIPTION OF APPLICATIONS

FIGS. 1A-I are schematic illustrations of several configurations of a needle assembly 20, in accordance with respective applications of the present invention. Needle assembly 20 comprises a needle 22 and a suture 24 coupled to needle 22, and a needle guide tool 30, which is configured to pass needle 22 and suture 24 through tissue of a body portion of a subject, such as described hereinbelow with reference to FIGS. 4A-F.

Figure 1A:
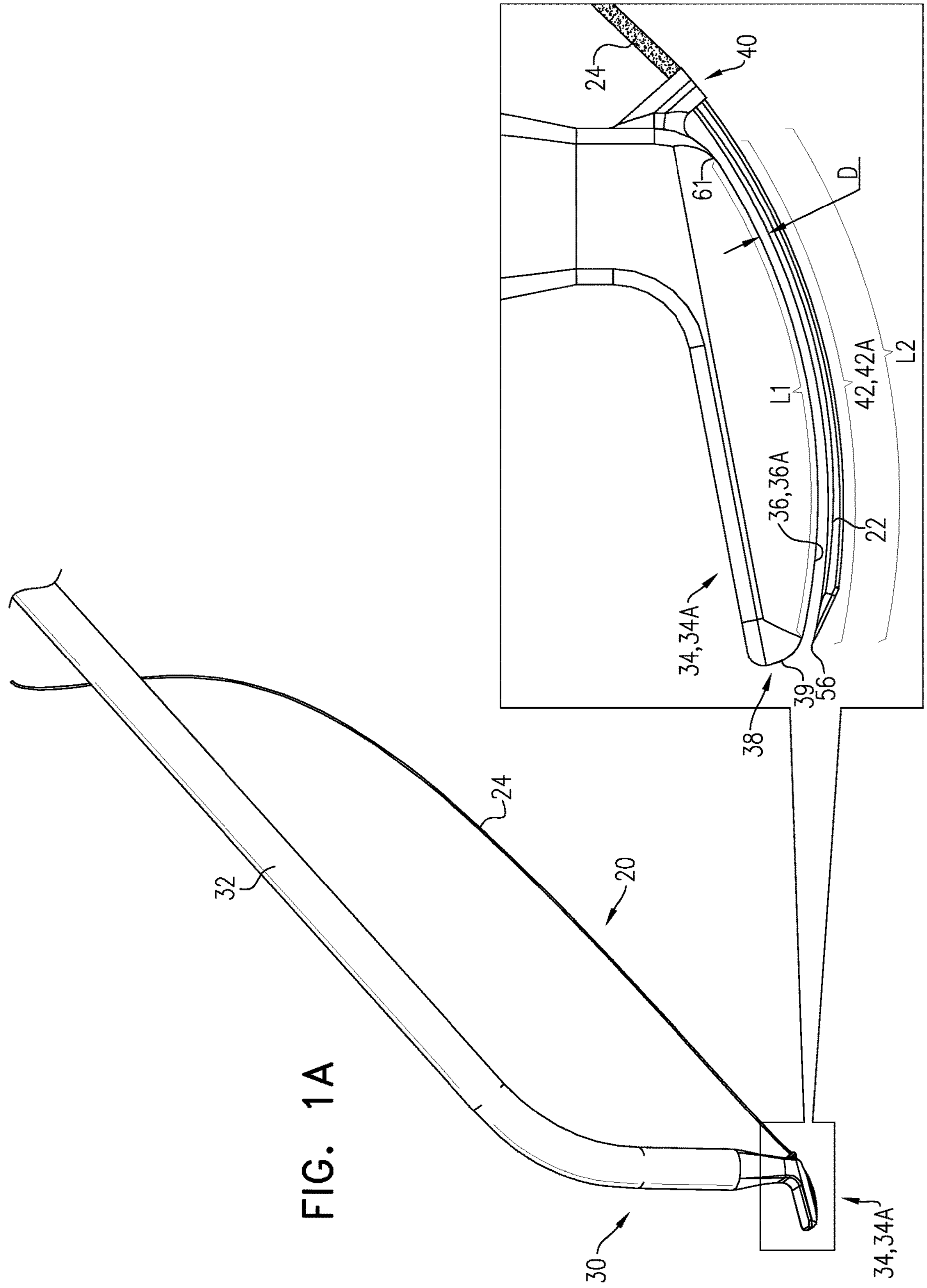
FIGS. 1A-I are schematic illustrations of several configurations of a needle assembly, in accordance with respective applications of the present invention.
Figure 1B:
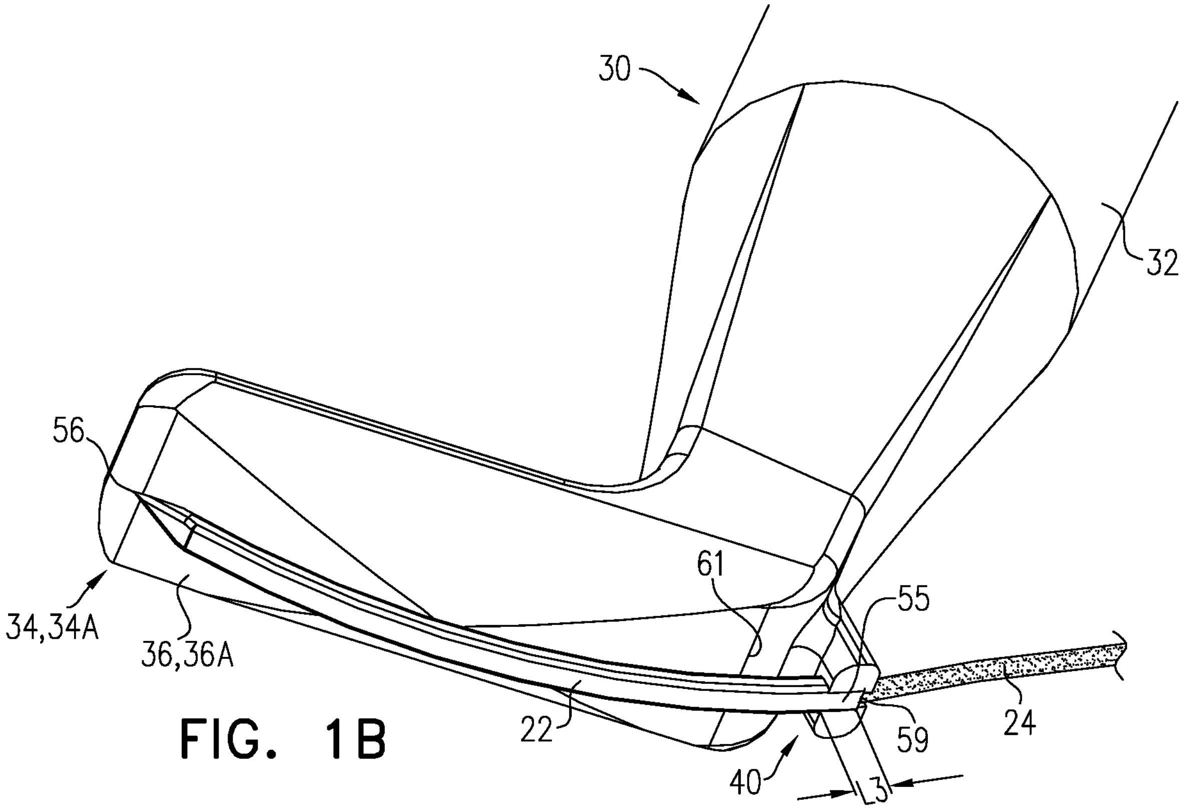
Figure 1C:
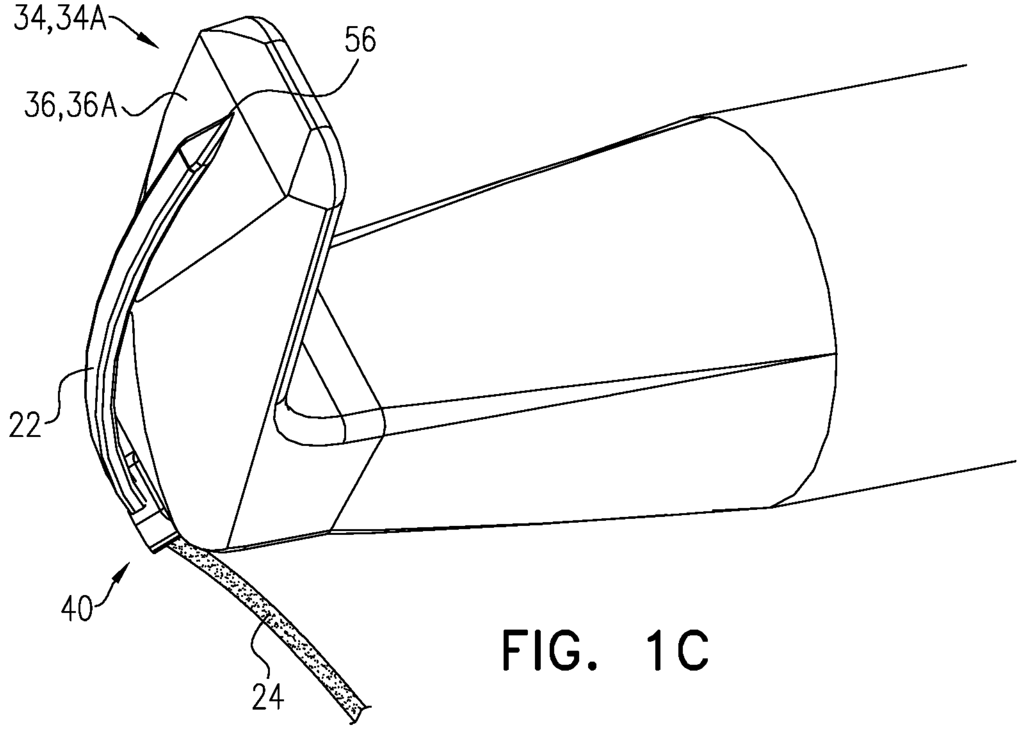

Needle guide tool 30 comprises:

- a needle guide 34, which is shaped so as to define a needle-guide surface 36 that is configured to slidably contact a body-portion surface of the body portion without penetrating the body-portion surface, such as described hereinbelow with reference to FIGS. 4A-F; and
- a proximal needle holder 40, which is disposed proximal to needle-guide surface 36 (and optionally proximal to needle guide 34), and which is configured to releasably hold needle 22 such that a longitudinal segment 42 (labeled in FIGS. 1A, 1E, and 1G) of needle 22 runs alongside needle-guide surface 36 at a non-zero distance D therefrom that does not vary along longitudinal segment 42 of needle 22, such as shown in FIGS. 1A-C. 1E-F, and 1G-I and labeled in FIGS. 1A, 1E, and 1G; as a result, longitudinal segment 42 of needle 22 is oriented parallel to needle-guide surface 36.

The non-zero distance D is less than the thickness of the tissue through which the needle is passed.

Typically, a lower surface of needle guide 34 is shaped so as to define needle-guide surface 36.

For some applications, such as for configurations in which the body portion includes a portion of an eye, such as a sclera, the non-zero distance D is equal to a value at least 0.1 mm, no more than 1 mm, and/or between 0.1 and 1 mm, such as at least 0.2 mm, no more than 0.4 mm, and/or between 0.2 and 0.4 mm.

Figure 1D:
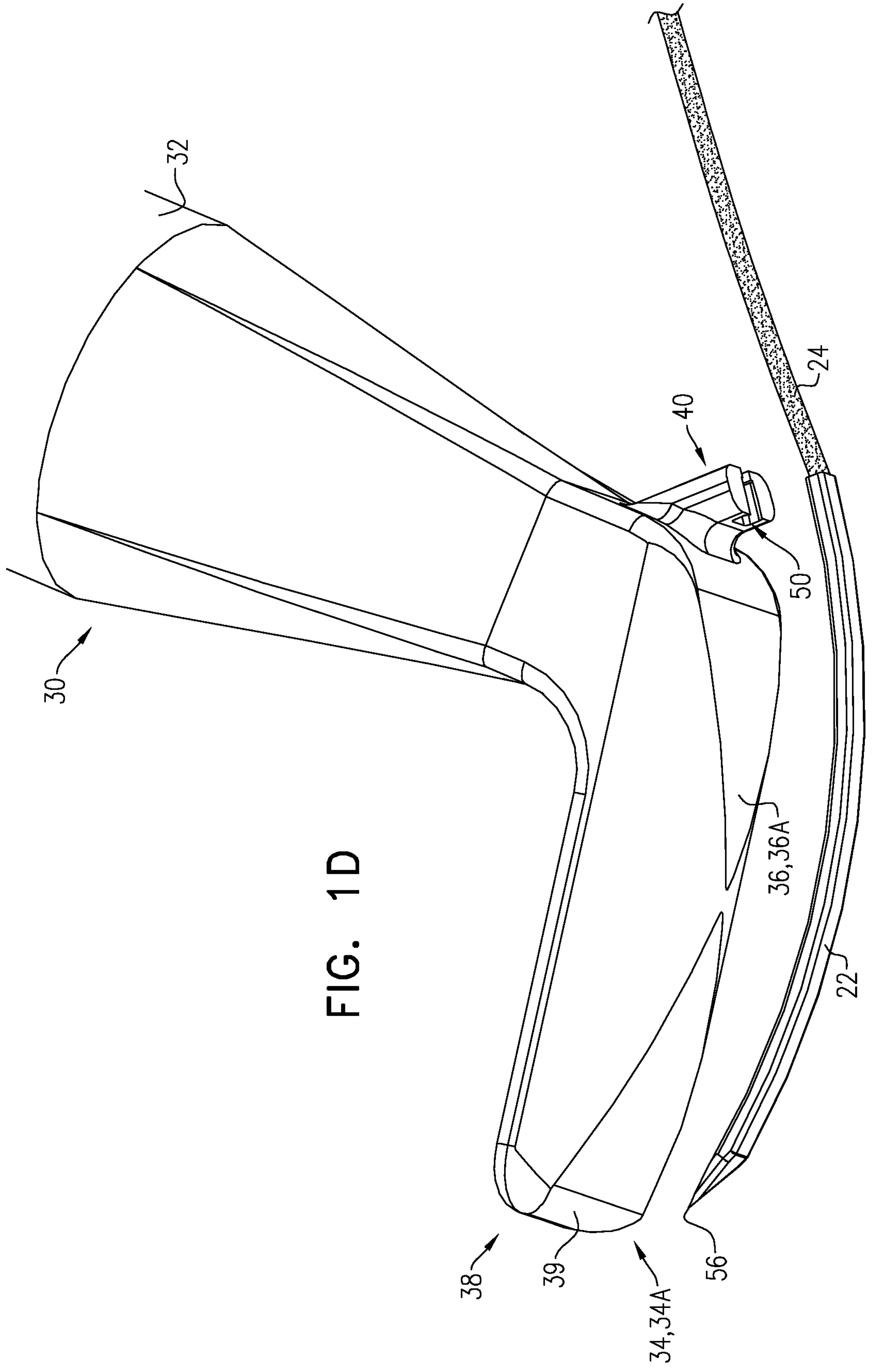

FIG. 1D shows a portion of needle assembly 20 after needle 22 has been released from proximal needle holder 40.

Typically, needle guide tool 30 further comprises a handle 32, which supports needle guide 34.

In the configuration shown in FIGS. 1A-D, needle guide tool 30 comprises a needle guide 34A, which is shaped so as to define a needle-guide surface 36A, and longitudinal segment 42 of needle 22 is a longitudinal segment 42A of needle 22. Needle guide 34A is one configuration of needle guide 34, and needle-guide surface 36A is one configuration of needle-guide surface 36.

Figure 1E:
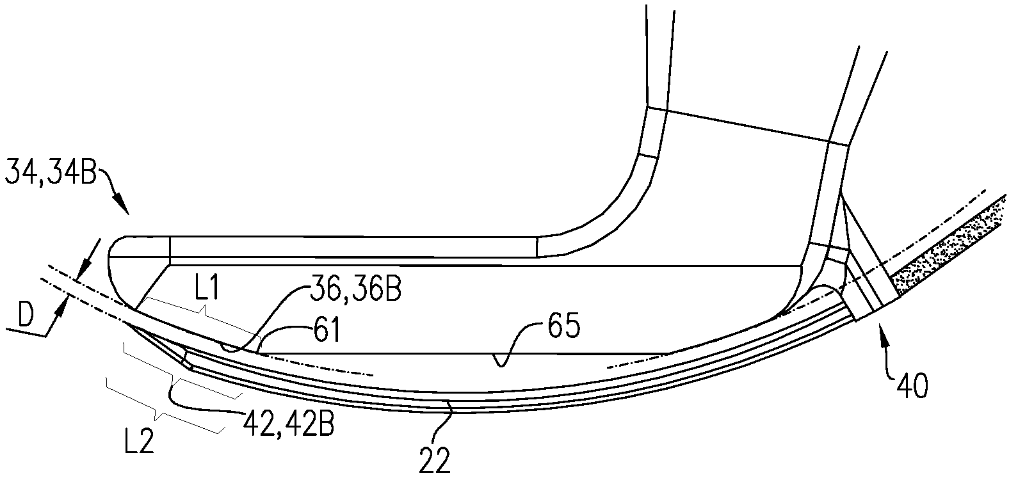
Figure 1F:
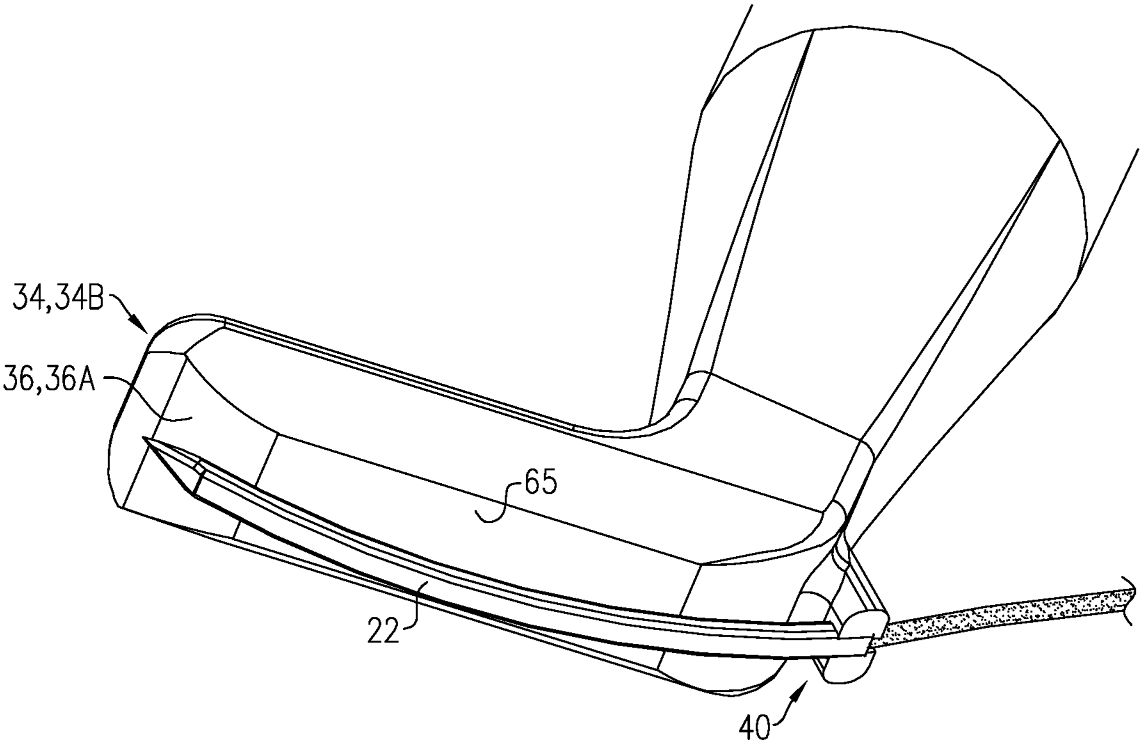

In the configuration shown in FIGS. 1E-F, needle guide tool 30 comprises a needle guide 34B, which is shaped so as to define a needle-guide surface 36B, and longitudinal segment 42 of needle 22 is a longitudinal segment 42B of needle 22. Needle guide 34B is one configuration of needle guide 34, and needle-guide surface 36B is one configuration of needle-guide surface 36.

Figure 1G:
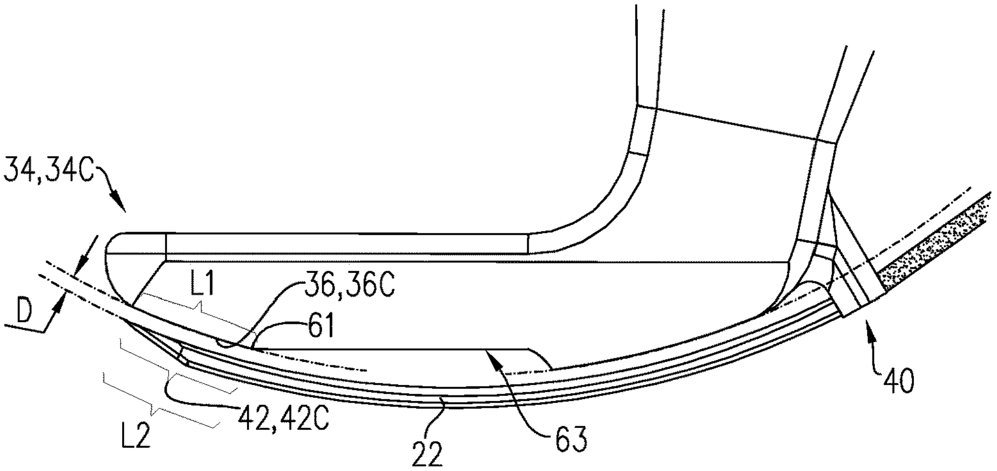
Figure 1H:
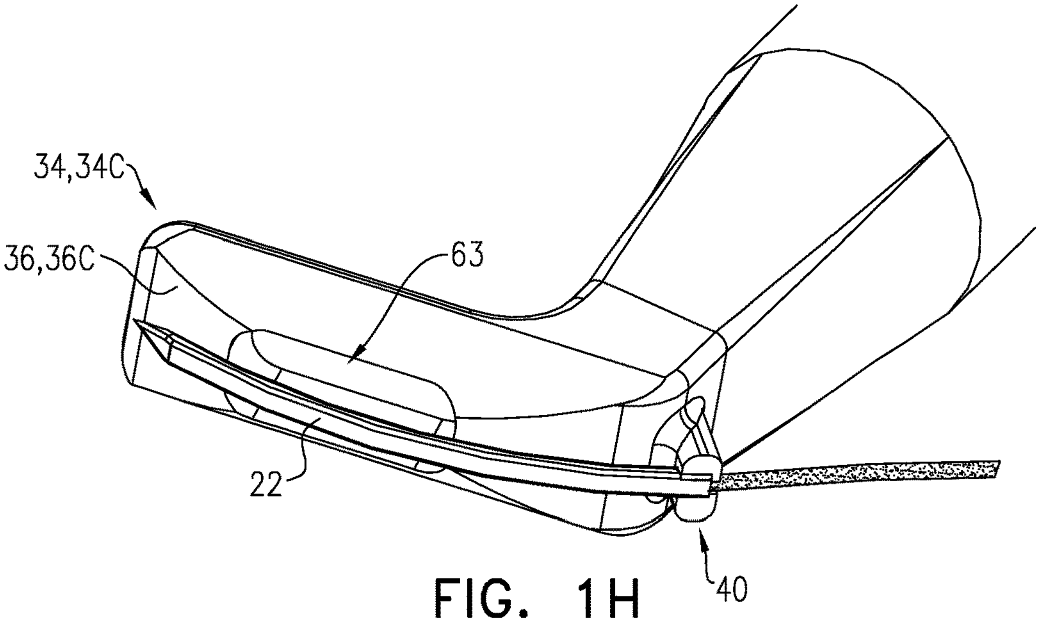
Figure 1I:
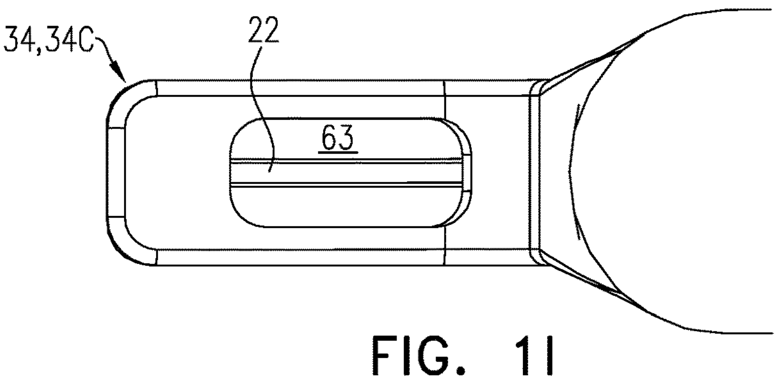

In the configuration shown in FIGS. 1G-I, needle guide tool 30 comprises a needle guide 34C, which is shaped so as to define a needle-guide surface 36C, and longitudinal segment 42 of needle 22 is a longitudinal segment 42C of needle 22. Needle guide 34C is one configuration of needle guide 34, and needle-guide surface 36C is one configuration of needle-guide surface 36. FIG. 11 is a top-view of needle guide 34C.

Reference is again made to FIGS. 1A-C, 1E-F, and 1G-I. Needle guide tool 30 is configured such that sliding of needle-guide surface 36 distally along the body-portion surface advances needle 22 within the body portion beneath the body-portion surface at a depth no more than the non-zero distance D, such as described hereinbelow with reference to FIGS. 4C-D (the precise definition of this depth is provided hereinbelow with reference to FIGS. 4C-D). More particularly, needle guide tool 30 is configured such that sliding of needle-guide surface 36 along the body-portion surface, while proximal needle holder 40 holds needle 22, penetrates a distal needle tip 56 of needle 22 through the external surface at a proximal site, passes distal needle tip 56 within the tissue, and passes distal needle tip

56 out of the external surface at a distal site distal to the proximal site, while needle guide 34 and needle 22 held by proximal needle holder 40 remain outside the body portion, and while needle-guide surface 36 slides along the body-portion surface.

For some applications, proximal needle holder 40 is configured to releasably hold needle 22 such that needle 22 is fixed with respect to needle guide 34 (but not necessarily longitudinally or rotationally fixed with respect to needle guide 34).

Typically, proximal needle holder 40 is configured to releasably hold needle 22 such that needle 22 is longitudinally fixed with respect to needle guide 34 (but not necessarily rotationally fixed with respect to needle guide 34).

As labeled in FIG. 1B, proximal needle holder 40 is configured to releasably hold needle 22 by directly contacting a longitudinal portion 55 of needle 22, without directly contacting any other portions of needle 22. For example, a length L3 of longitudinal portion 55 may between 5 and 20% of the length of needle 22.

Typically, needle guide tool 30 is configured such that the sliding of needle-guide surface 36 distally along the body-portion surface, while needle 22 is entirely exposed except along longitudinal portion 55 of needle 22, advances needle 22 within the body portion beneath the body-portion surface at a depth no more than the non-zero distance D (the precise definition of this depth is provided hereinbelow with reference to FIGS. 4C-D).

Typically, a proximal end 59 of needle 22 (labeled in FIG. 1B) is located proximal to a proximal end 61 of needle-guide surface 36 (labeled in FIGS. 1A-B, 1E, and 1G) when needle 22 is held by proximal needle holder 40.

For some applications, needle 22 is curved, such as shown in FIGS. 1A-I (and FIGS. 4A-F, 5A-D, and 6A-D). For these applications, needle-guide surface 36 is correspondingly convexly curved along a curved longitudinal axis thereof parallel to needle 22 when needle 22 is held by proximal needle holder 40. Optionally, needle 22 and needle-guide surface 36 have a radius of curvature of between 2.5 and 7 mm, such as between 3 and 5 mm.

For other applications, needle 22 is straight, such as described hereinbelow with reference to FIGS. 2, 7A-B, and 8A-B.

Reference is still made to FIGS. 1A-I. Typically, needle-guide surface 36 has a length L1 (labeled in FIGS. 1A, 1E, and 1G) of at least 1.5 mm, such as at least 2 mm. Such a length typically allows needle 22 to pass within the tissue without penetrating through the tissue to adjacent tissue beneath the tissue. (For applications in which needle-guide surface 36 is curved, the length L1 is measured along the curvature of the surface, rather than as a straight line between the ends of the surface.)

Reference is made to FIGS. 1A-D. In this configuration, needle-guide surface 36A may extend along nearly an entire length of the lower surface of needle guide 34A, such as along at least 80%, e.g., at least 90% of the lower surface. In this configuration, length L1 of needle-guide surface 36A typically equals at least 40% (e.g., at least 60%), no more than 120% (e.g., no more than 110%, such as no more than 90%), and/or between 40% and 120% of the length of the needle, such as between 60% and 90% of the length of needle 22. Such a length typically allows needle 22 to pass within the tissue without penetrating through the tissue to adjacent tissue beneath the tissue.

Reference is made to FIGS. 1E-F. In this configuration, needle-guide surface 36B extends along substantially less than an entire length of the lower surface of needle guide 34B, such as along less than 50%, e.g., less than 25% of the entire length of the lower surface of needle guide 34B. For example, the lower surface of needle guide 34B may be shaped so as to define at least one other portion 65 that does not define needle-guide surface 36B, and may be straight (such as shown), concave (configuration not shown), or another shape (other portion 65 thus does not run alongside needle 22 at the non-zero distance D from needle-guide surface 36B). In this configuration, length L1 of needle-guide surface 36B typically equals at least 10% (e.g., at least 15), no more than 50% (e.g., no more than 40%), and/or between 10% and 50% of the length of the needle, such as between 15% and 40% of the length of needle 22. Such a length typically allows needle 22 to pass within the tissue without penetrating through the tissue to adjacent tissue beneath the tissue.

Reference is made to FIGS. 1G-I. In this configuration, needle-guide surface 36C extends along substantially less than an entire length of the lower surface of needle guide 34C, such as along less than 50%, e.g., less than 25% of the entire length of the lower surface of needle guide 34C. Needle guide 34C may be shaped so as to define a window 63 that passes through needle guide 34C from an upper surface to a lower surface of needle guide 34C. Window 63 may define proximal end 61 of needle-guide surface 36C. Window 63 does not define needle-guide surface 36C (window 63 thus may not run alongside needle 22 at the non-zero distance D from needle-guide surface 36C). In this configuration, length L1 of needle-guide surface 36C typically equals at least 10% (e.g., at least 15), no more than 50% (e.g., no more than 40%), and/or between 10% and 50% of the length of the needle, such as between 15% and 40% of the length of needle 22. Such a length typically allows needle 22 to pass within the tissue without penetrating through the tissue to adjacent tissue beneath the tissue. Window 63 may allow viewing of a portion of needle 22 during the procedure.

The device may utilize the difference in properties of the various tissues. For example, the eyeball itself is a relatively compressible, while the sclera is relatively rigid, thus the area through which the suture is passed becomes flat, but the rigid features of the sclera allow controlled penetration thickness.

Longitudinal segment 42 of needle 22 has a length L2 (labeled in FIGS. 1A, 1E, and 1G), when needle 22 is held by proximal needle holder 40, that depends on the length of penetration required; for example, for use in the sclera, the length L2 may be at least 1.5, such as at least 2 mm (for applications in which needle 22 is curved, the length L2 is measured along the curvature of the needle, rather than as a straight line between the ends of the longitudinal segment). Length L2 typically corresponds with length L1 of needle-guide surface 36, described hereinabove. Alternatively or additionally, for some applications, longitudinal segment 42 of needle 22 includes an entirety of needle 22 that runs alongside needle-guide surface 36, when needle 22 is held by proximal needle holder 40.

Reference is again made to FIGS. 1A-I. Typically, needle 22 comprises a proximal swage to which suture 24 is coupled, as is known in the surgical needle art. Alternatively, needle 22 comprises another connector, such as an eyelet, to which suture 24 is coupled (configuration not shown, but known in the surgical needle art). For applications in which needle 22 comprises a proximal swage or another connector, the length of needle 22, which is described hereinabove in relation to the length L1 of needle-guide surface 36, includes the swage or other connector.

Optionally, needle 22 has a length of between 6 and 8 mm, such as 7 mm.

For some applications, needle 22 is solid, while for other application, needle 22 is hollow, such as for configurations in which suture 24 is not coupled to needle 22, and is instead passed through a lumen of the needle 22 after needle 22 is passed through the tissue. The independent suture is then passed through the hollow needle, and the hollow needle is removed from the tissue by proximally withdrawing the hollow needle, typically using proximal needle holder 40. (Typically, the suture is connected to a guide that is not sharp, but more rigid than suture, for guiding the suture through the hollow needle).

For some applications, needle guide 34, at a distal end portion 38 thereof distal to needle-guide surface 36, is shaped so as to define a curved surface 39 that faces partially in a distal direction and partially toward the body-portion surface when needle-guide surface 36 slidably contacts the body-portion surface. One function of curved surface 39 is described hereinbelow with reference to FIGS. 4B-C.

Typically, needle guide tool 30 is not shaped so as to define any passages through which any portions of needle 22 or suture 24 pass when needle 22 is held by proximal needle holder 40.

Typically, needle guide tool 30 is not shaped so as to define any passages in which any portion of needle 22 is disposed when needle 22 is held by proximal needle holder 40.

Typically, needle guide tool 30 is not shaped so as to define any passages through which any portion of needle 22 is slidable when needle 22 is held grasped by proximal needle holder 40.

For some applications, at least a portion of (such as an entirety of) needle guide 34 is transparent or translucent to allow viewing of needle 22 during entry into and/or exit out of the tissue, and/or viewing of the path of the needle beneath the surface, which can be indirectly observed because of the needle's motion as it passes through the tissue.

Figure 2:
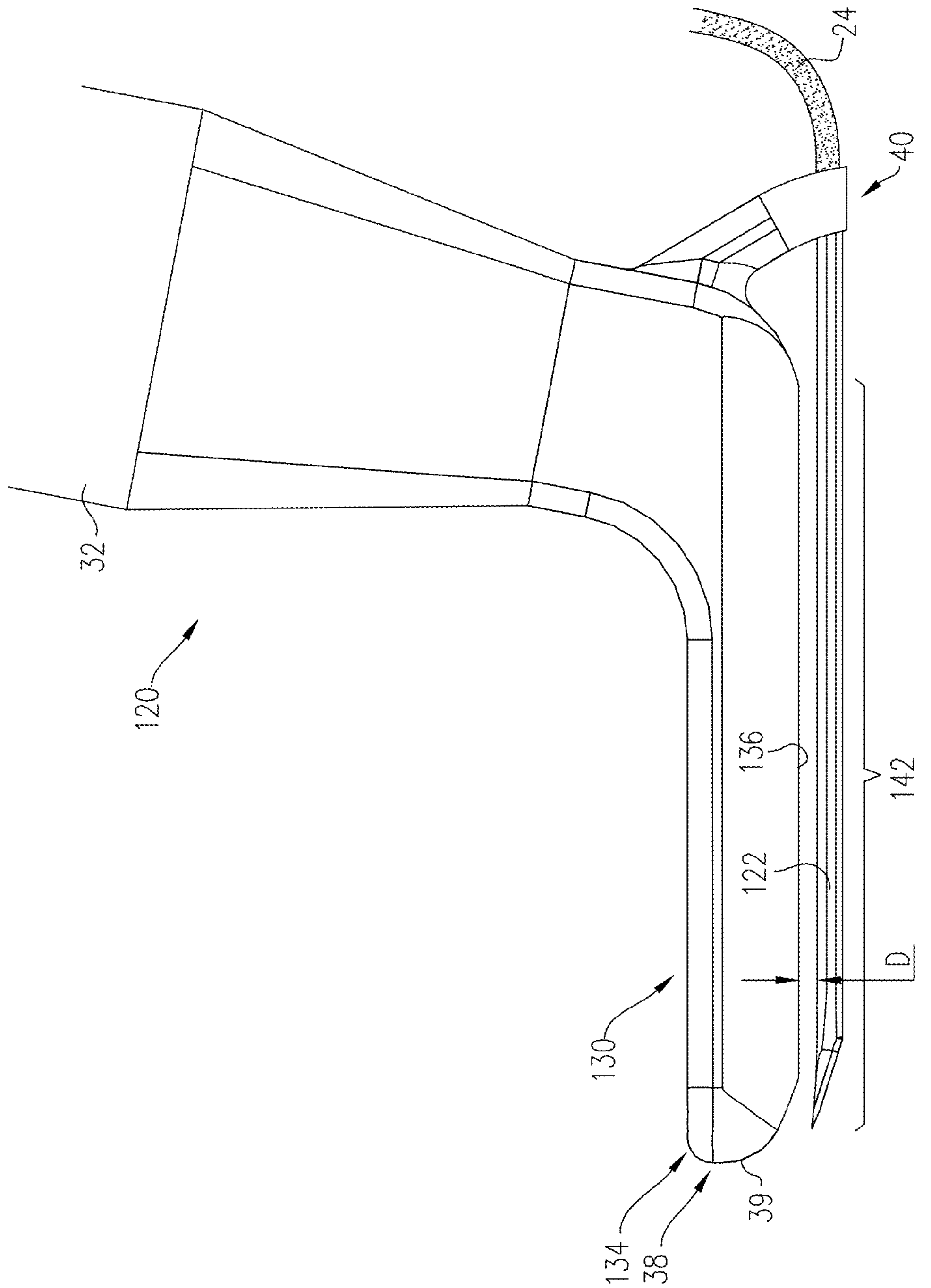
FIG. 2 is a schematic illustration of another needle assembly, in accordance with an application of the present invention.

Reference is now made to FIG. 2, which is a schematic illustration of a needle assembly 120, in accordance with an application of the present invention. Except as described below, needle assembly 120 is similar to needle assembly 20, described hereinabove with reference to FIGS. 1A-I, and may implement any of the techniques described with reference thereto, mutatis mutandis. Similarly, needle assembly 20 may implement any of the techniques described with reference to needle assembly 120, mutatis mutandis.

Needle assembly 120 comprises a needle 122 and suture 24 coupled to needle 122. Needle assembly 120 further comprises a needle guide tool 130, which is configured to pass needle 122 and suture 24 through tissue of a body portion of a subject, such as described hereinbelow with reference to FIGS. 4A-F. Needle guide tool 130 may implement any of the features of needle guide tool 30, described hereinabove with reference to FIGS. 1A-I.

Proximal needle holder 40 of needle guide tool 130 is configured to releasably hold needle 122 such that a longitudinal segment 142 of needle 122 runs alongside a needle-guide surface 136 of a needle guide 134 of needle guide tool 130 at the non-zero distance D therefrom that does not vary along longitudinal segment 142 of needle 122.

Needle 122 is straight, and straight longitudinal segment 142 is oriented parallel to needle-guide surface 136, which is also straight. For these applications, needle-guide surface 36 is straight along a straight longitudinal axis thereof parallel to needle 122 when needle 122 is held by proximal needle holder 40, such as described hereinbelow with reference to FIGS. 3A-E.

Figure 3A:
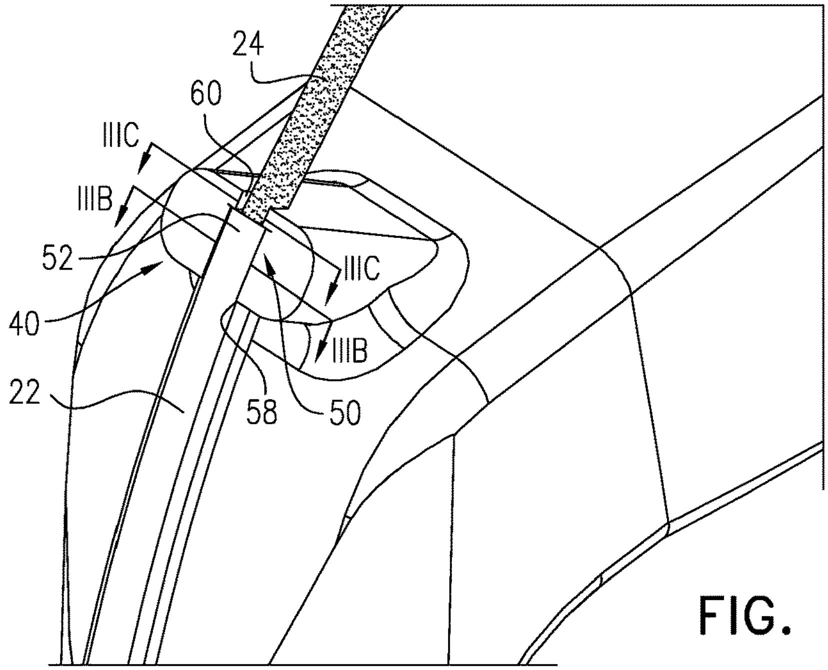
FIGS. 3A-E are schematic illustrations of one configuration of a proximal needle holder of a needle guide tool of the needle assemblies of FIGS. 1A-D and 2, in accordance with an application of the present invention.
Figure 3B:
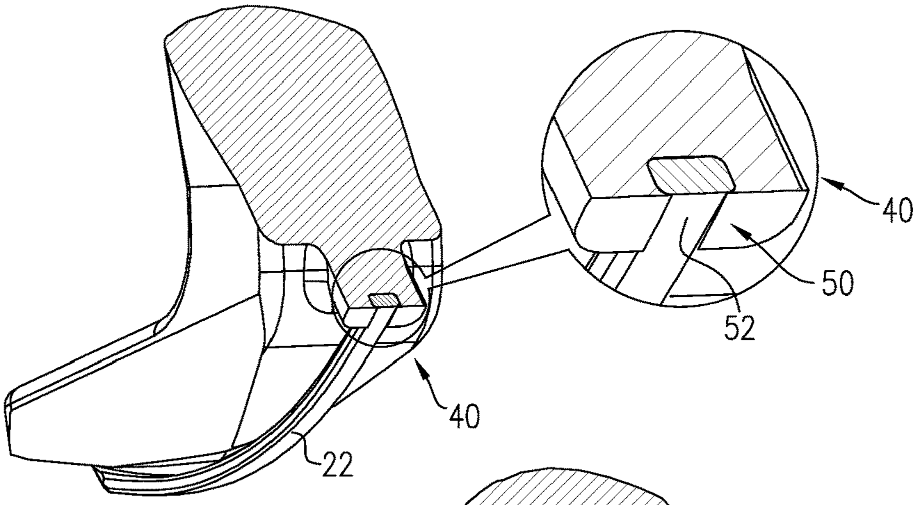
Figure 3C:
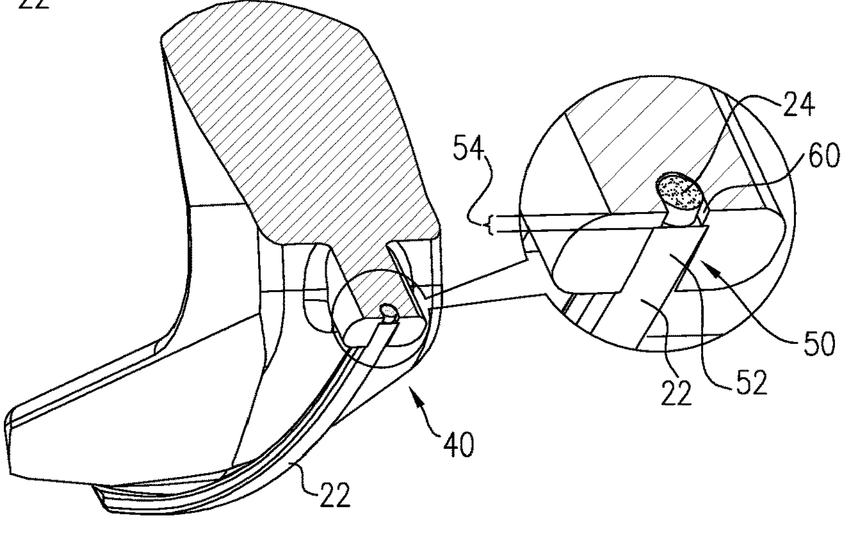
Figure 3D:
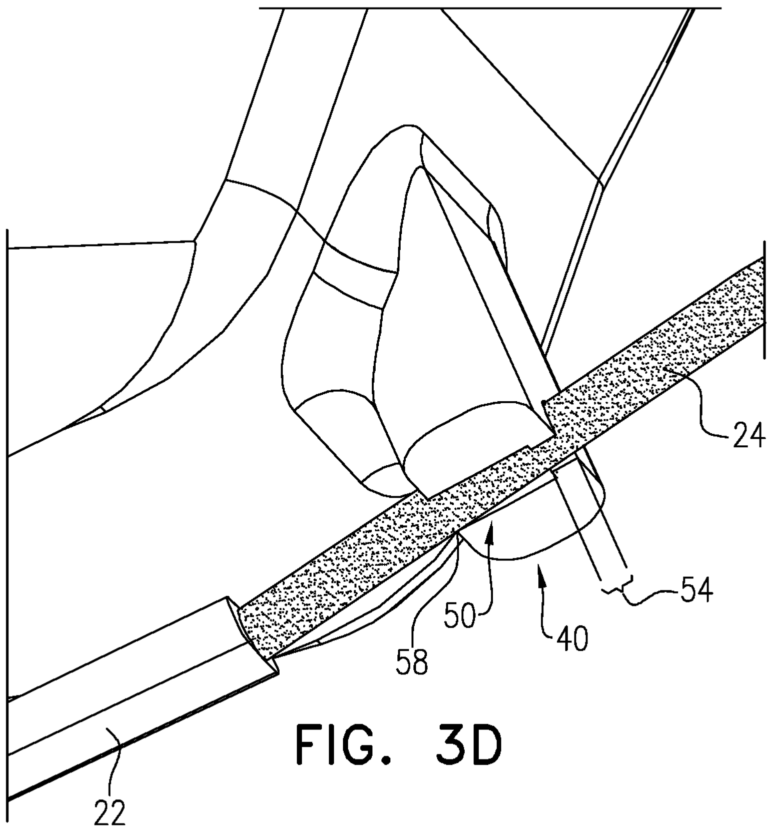
Figure 3E:
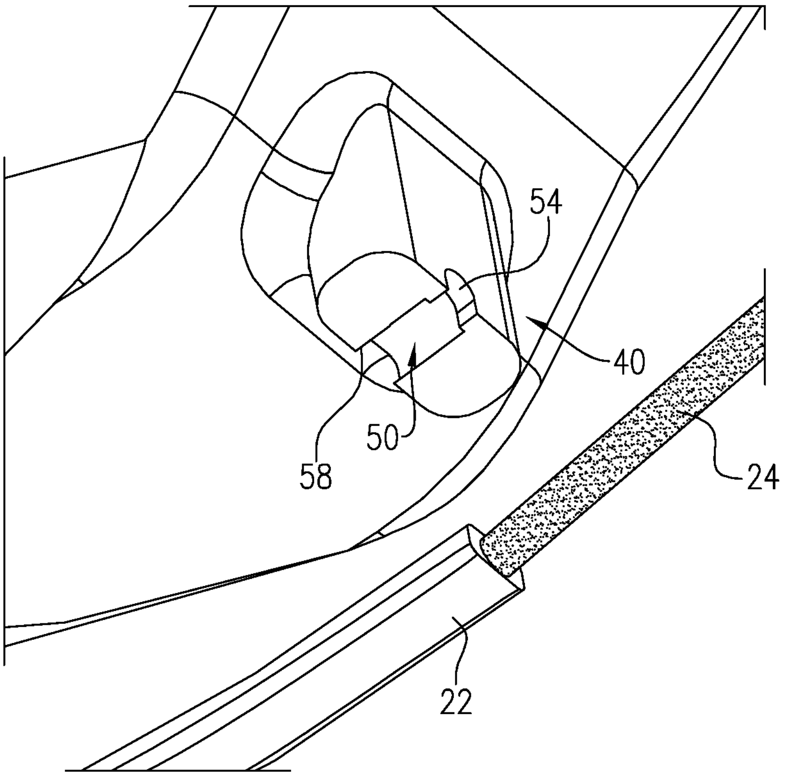

Reference is now made to FIGS. 3A-E, which are schematic illustrations of one configuration of proximal needle holder 40, in accordance with an application of the present invention. FIG. 3A shows needle 22 held by proximal needle holder 40. FIGS. 3B and 3C are cross-sectional views taken along lines IIIB-IIIB and IIIC-IIIC of FIGS. 3A, respectively. FIGS. 3D-E show the release of needle 22 from proximal needle holder 40, as describe below.

In this configuration, as shown in FIGS. 3A-C, proximal needle holder 40 is shaped so as to define a passage 50 in which a longitudinal portion 52 of needle 22 is releasably disposed, such that proximal needle holder 40 releasably holds needle 22. For example, longitudinal portion 52 of needle 22 may be snugly disposed within passage 50, so as to prevent rotation of needle 22 with respect to proximal needle holder 40.

For some applications, a proximal portion 54 of passage 50 is narrower than needle 22, such that sliding of needle-guide surface 36 distally along the body-portion surface causes proximal portion 54 of passage 50 to distally push needle 22 through the body portion, such as described hereinbelow with reference to FIGS. 4C-D. After distal needle tip 56 has exited the body-portion surface, such as described hereinbelow with reference to FIG. 4D, needle 22 can be released from proximal needle holder 40 by distally pulling longitudinal portion 52 of needle 22 out of a distal end 58 of passage 50, as shown in FIG. 3D.

For some applications, passage 50 is shaped so as to define a longitudinal slot 60, labeled in FIGS. 3A and 3C, which is narrower than longitudinal portion 52 of needle 22, such that longitudinal portion 52 of needle 22 cannot pass through longitudinal slot 60. Longitudinal slot 60 is wider than suture 24, such that once needle 22 has been released from proximal needle holder 40 by distally pulling longitudinal portion 52 of needle 22 out of distal end 58 of passage 50, proximal needle holder 40 can be removed from suture 24, such as shown in FIG. 3E, allowing the entire needle guide tool 30 to be disengaged from the tissue of the body portion, such as described hereinbelow with reference to FIG. 4E.

Reference is now made to FIGS. 4A-F, which are schematic illustrations of a method for passing, through tissue 70 of a body portion 72 of a subject, needle 22 and suture 24 coupled to needle 22, in accordance with an application of the present invention. Although the method is illustrated using needle guide tool 30, described hereinabove with reference to FIGS. 1A-I and 2A-E, the method may also be performed using needle guide tools 130, 230, and 330, described herein with reference to FIG. 2; FIGS. 5A-D and 6A-D; and FIGS. 7A-B and 8A-B, respectively, mutatis mutandis.

In the exemplary method illustrated in FIGS. 4A-F, body portion 72 includes a portion of an eye 80, tissue 70 includes sclera 82 of eye 80, and a body-portion surface 74 of the portion of eye 80 is a surface 84 of sclera 82 (the conjunctiva is removed before this surgical step) of eye 80. The method may alternatively be performed on another portion of eye 80; for example, tissue 70 may include a cornea. The method may further alternatively be performed on other non-eye tissue, such as a nerve (e.g., during microsurgery) or skin (e.g., during delicate skin suturing).

Figure 4A:
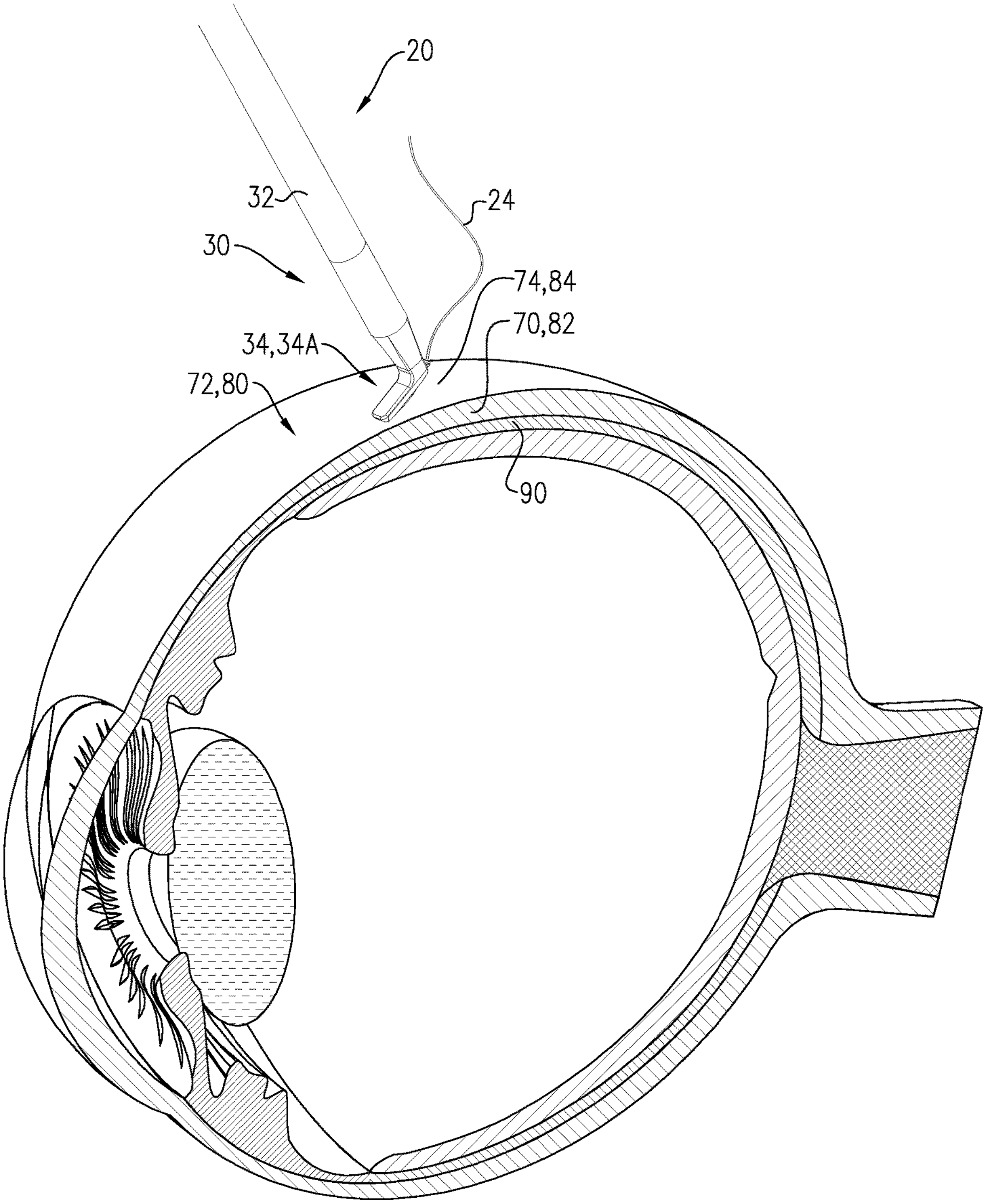
FIGS. 4A-F are schematic illustrations of a method for passing a needle and a suture through tissue of a body portion of a subject, using a needle guide tool of the needle assembly of FIGS. 1A-D, in accordance with an application of the present invention.
Figure 4B:
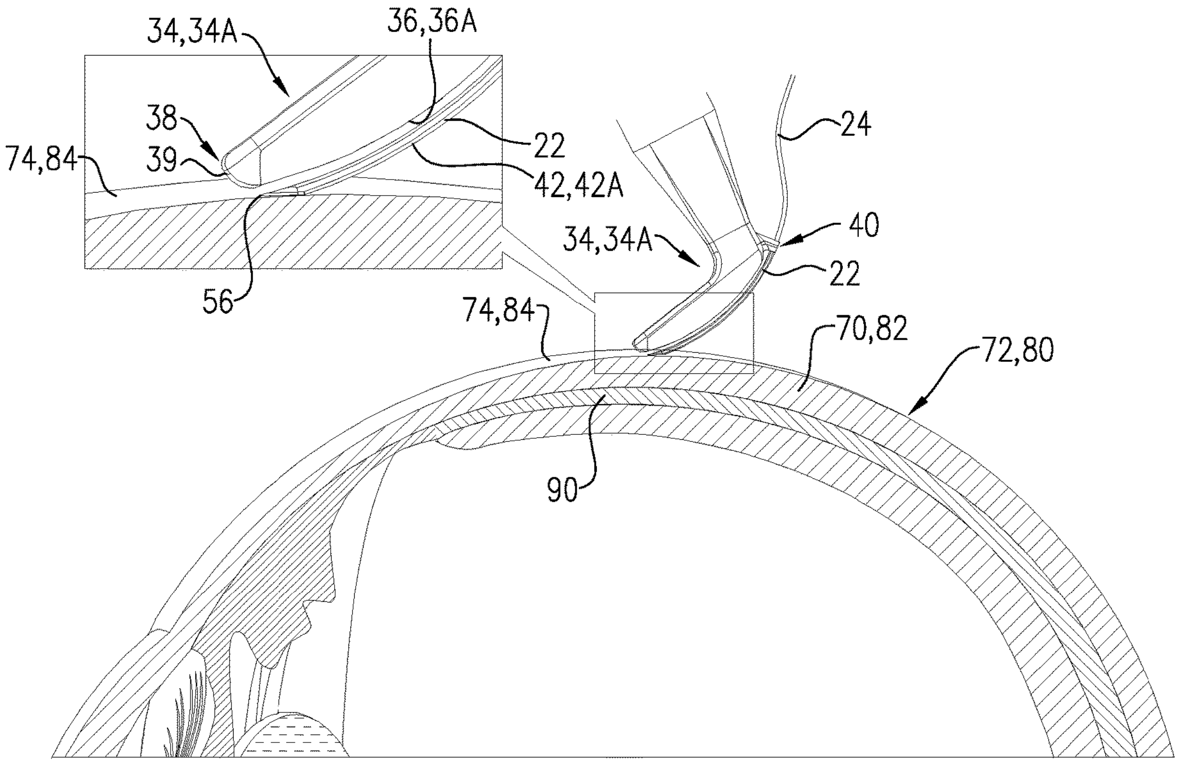

As shown in FIGS. 4A-B, using handle 32 of needle guide tool 30 (in configurations in which handle 32 is provided), needle guide 34 is positioned such that needle-guide surface 36 of needle guide 34 contacts body-portion surface 74 of body portion 72, while proximal needle holder 40 of needle guide tool 30 holds needle 22 such that longitudinal segment 42 of needle 22 runs alongside needle-guide surface 36 at the non-zero distance D therefrom that does not vary along longitudinal segment 42 of needle 22.

Figure 4C:
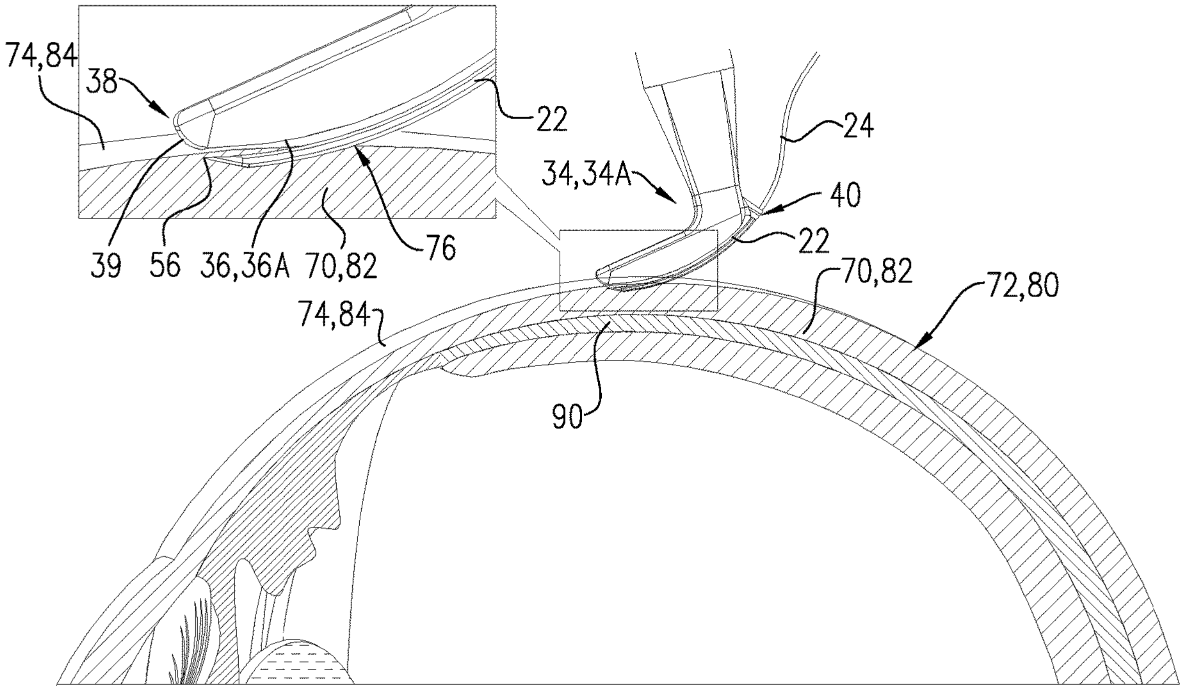
Figure 4D:
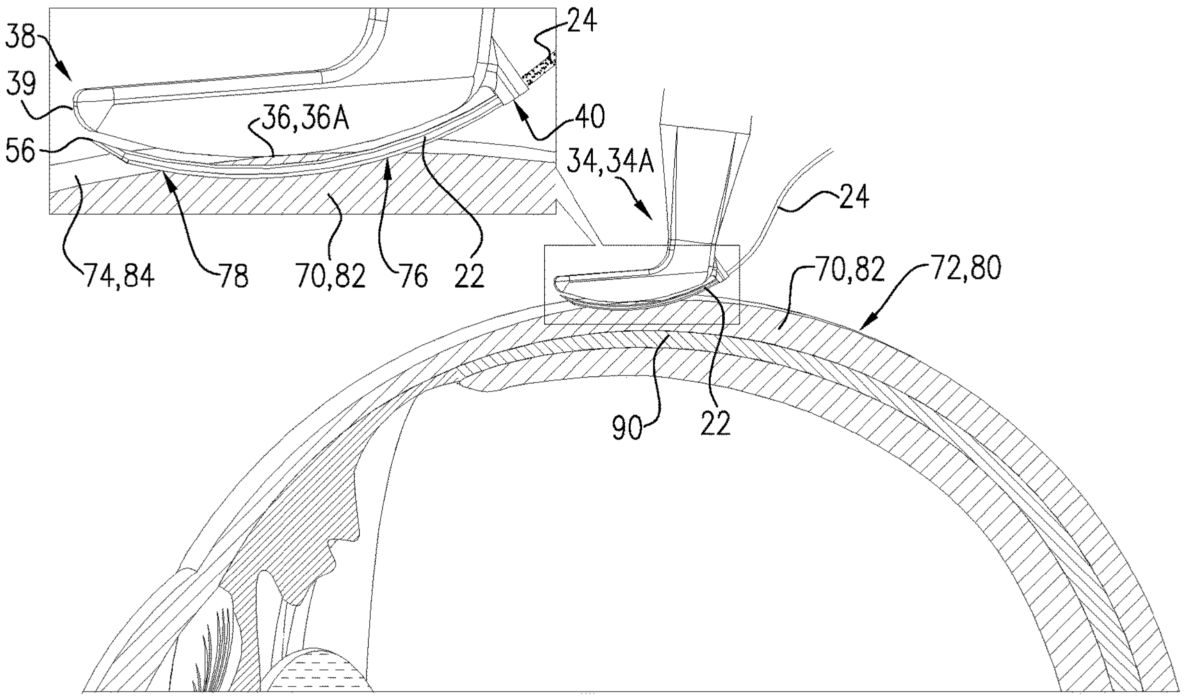

As shown in FIGS. 4C-D, needle-guide surface 36 is slid distally along body-portion surface 74 (e.g., sclera 82), thereby advancing needle 22 within body portion 72 (e.g., a portion of eye 80) beneath body-portion surface 74 at a depth D no more than the non-zero distance D. The depth D is measured between body-portion surface 74 and an edge of needle 22 closest to body-portion surface 74; the opposite edge of needle 22 farthest from body-portion surface 74 is disposed at a depth from body-portion surface 74 equal to the non-zero distance D plus the thickness of needle 22, measured in the direction of the measurement of the depth.

More particularly, needle-guide surface 36 is slid distally along body-portion surface 74 such that distal needle tip 56:

- penetrates body-portion surface 74 (e.g., sclera 82) at a proximal site 76, as shown in FIG. 4C,
- passes within tissue 70 (e.g., sclera 82) beneath body-portion surface 74 at the depth D no more than the non-zero distance D, as shown in FIGS. 4C-D, and
- exits body-portion surface 74 at a distal site 78 distal to proximal site 76, while needle guide 34 and needle 22 held by proximal needle holder 40 remain outside body portion 72, as shown in FIG. 4D, and while needle-guide surface 36 slides along body-portion surface 74.

Typically, the non-zero distance D is less than a thickness T of tissue 70, such as less than 85% of the thickness T of tissue 70, such that when needle-guide surface 36 distally slides along body-portion surface 74, distal needle tip 56 passes within tissue 70 beneath body-portion surface 74 at the depth D no more than the non-zero distance D without penetrating through tissue 70 to adjacent tissue 90 (e.g., the choroid) beneath tissue 70 (the precise definition of this depth is provided hereinabove).

Figure 4E:
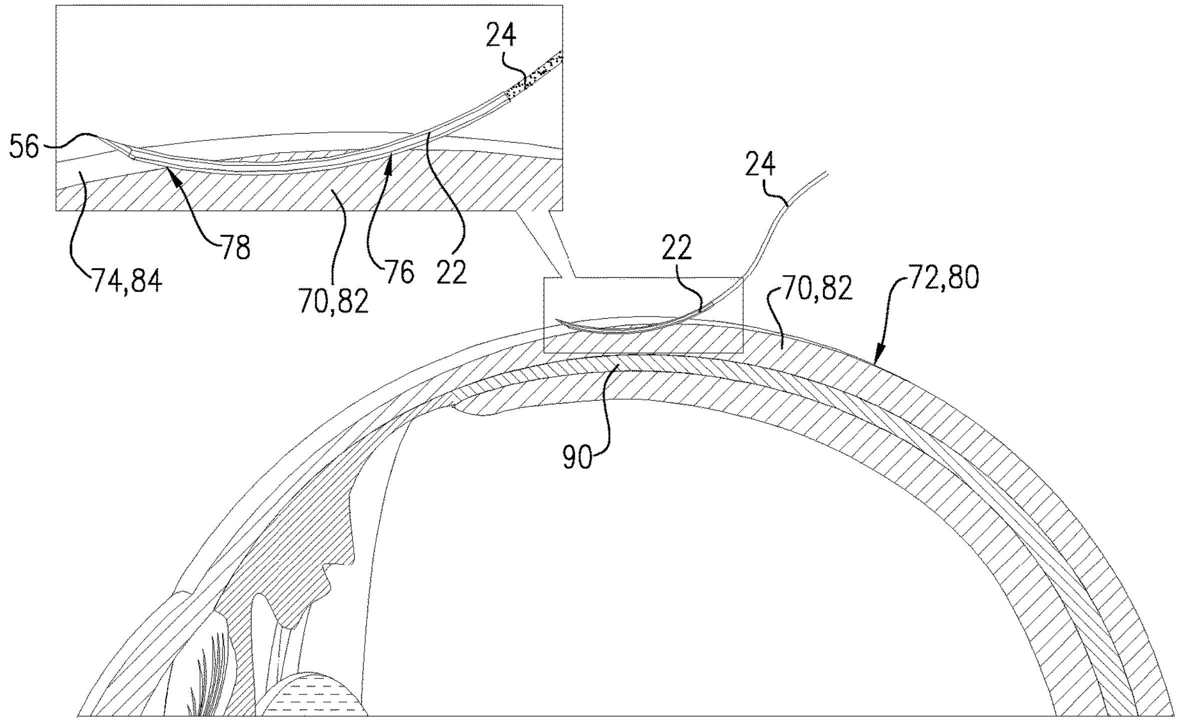

For some applications, as needle-guide surface 36 is slid distally along body-portion surface 74 (e.g., sclera 82 of eye 80), as shown in FIGS. 4C-E, the surgeon applies pressure to needle-guide surface 36, so as to partially locally compress body-portion surface 74 (e.g., sclera 82 of eye 80), thereby at least partially (e.g., entirely) conforming the shape of the body-portion surface to the shape of needle-guide surface 36 (i.e., either straight or curved). Such compression may aid in accurately controlling the depth of needle 22 beneath body-portion surface 74 at a known, fixed depth of penetration with respect to the surface of the body portion. As a result, the surgeon does not need to know or take into account the exactly geometry of body-portion surface 74. The device may utilize the difference in properties of the various tissues. For example, the eyeball itself is a relatively compressible, while the sclera is relatively rigid, thus the area through which the suture is passed becomes flat, but the rigid features of the sclera allow controlled penetration thickness.

As described hereinabove with reference to FIGS. 1A-I, proximal end 59 of needle 22 is typically located proximal to proximal end 61 of needle-guide surface 36 when needle 22 is held by proximal needle holder 40. As a result, no portion of needle-guide surface 36 proximally trails needle 22 as needle-guide surface 36 is slid distally along body-portion surface 74.

Thereafter, needle 22 is released from proximal needle holder 40, resulting in the freed needle shown in FIG. 4E.

Figure 4F:
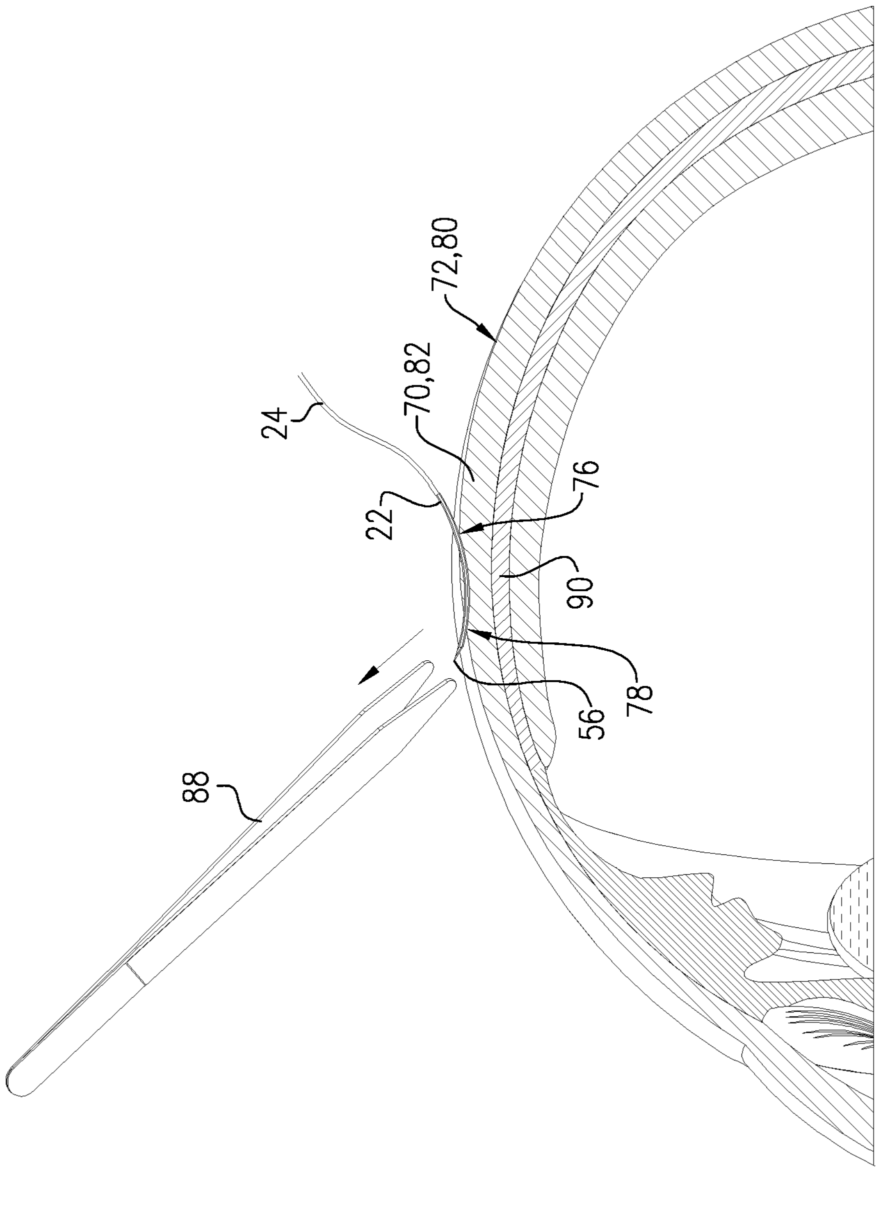
Figure 5A:
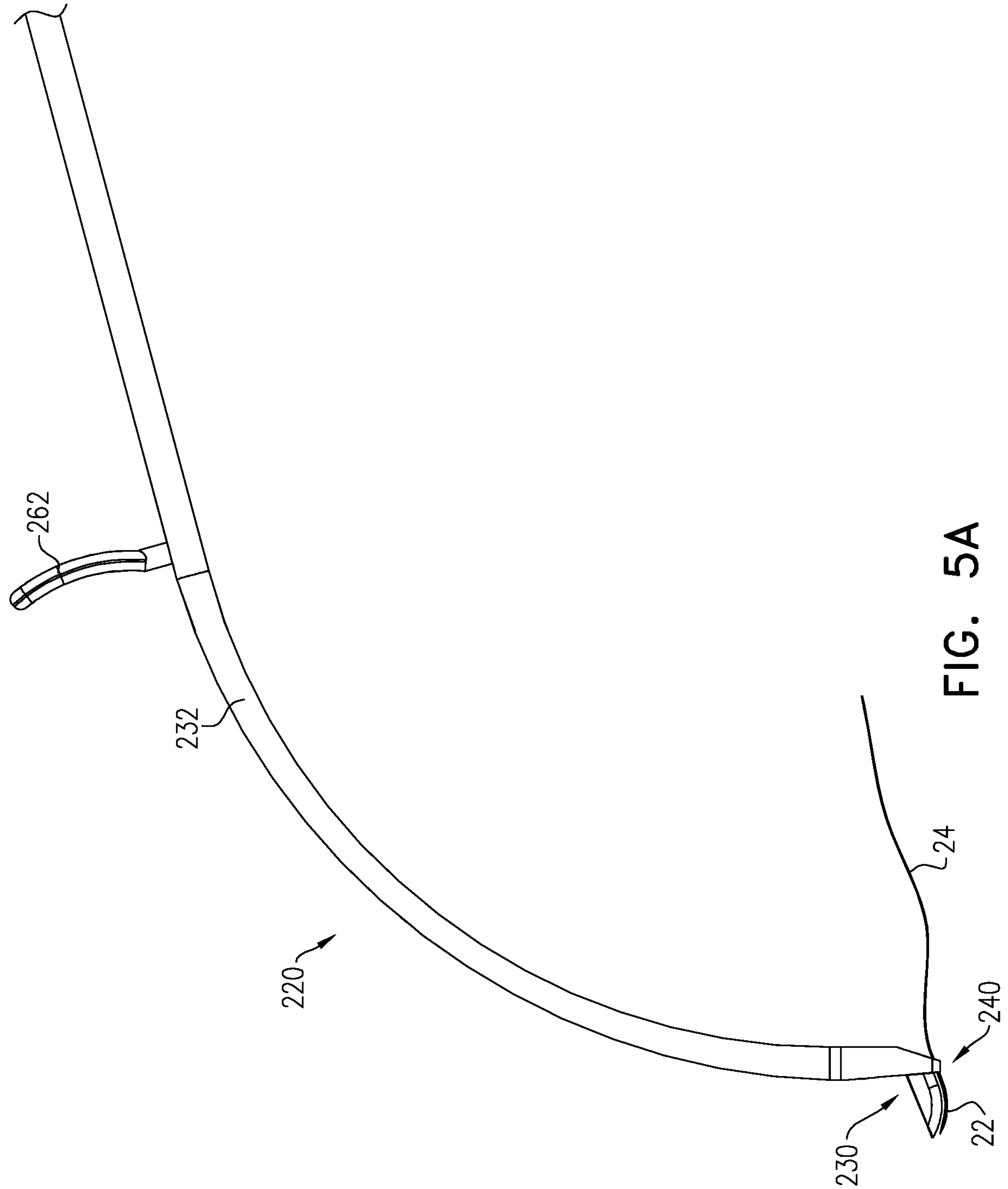
FIGS. 5A-D are schematic illustrations of yet another needle assembly in a grasping state, in accordance with an application of the present invention.
Figure 5B:
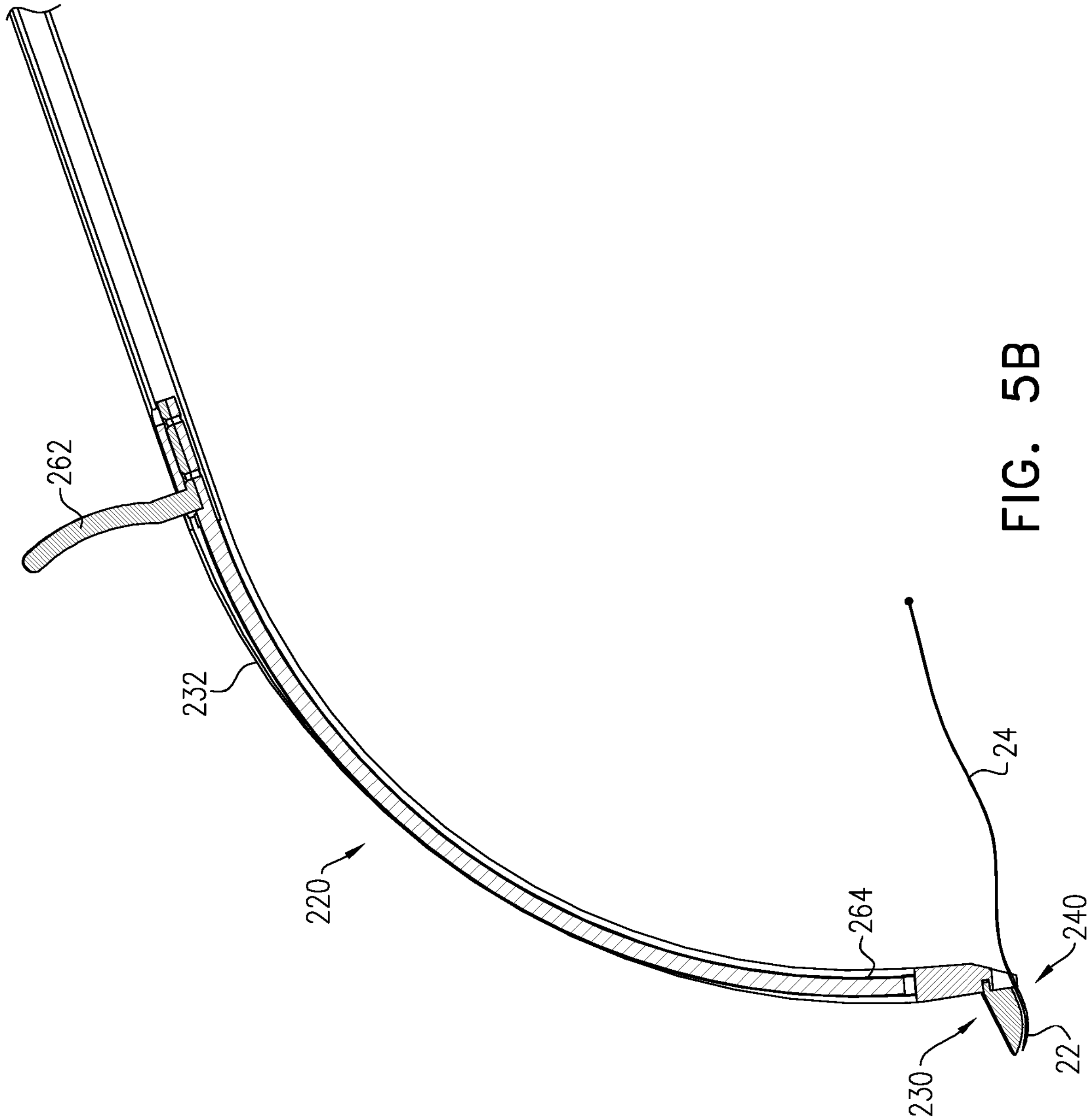
Figure 5C:
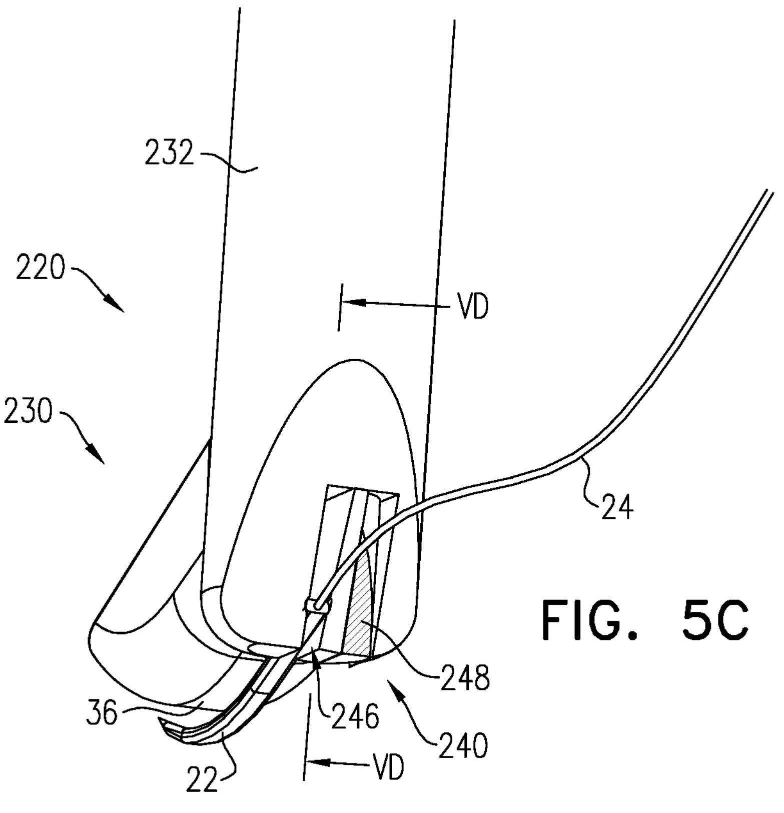
Figure 5D:
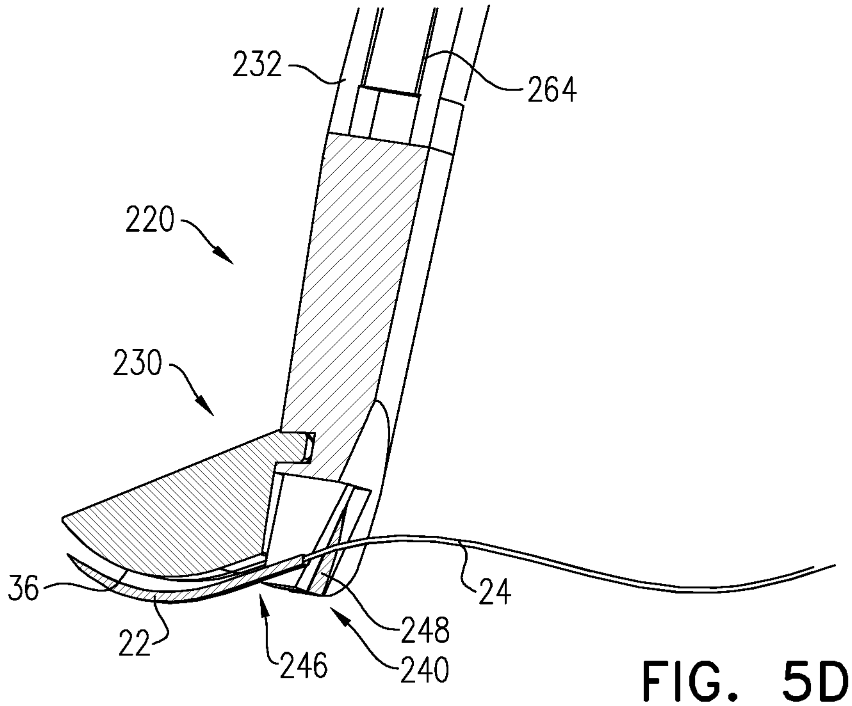
Figure 6A:
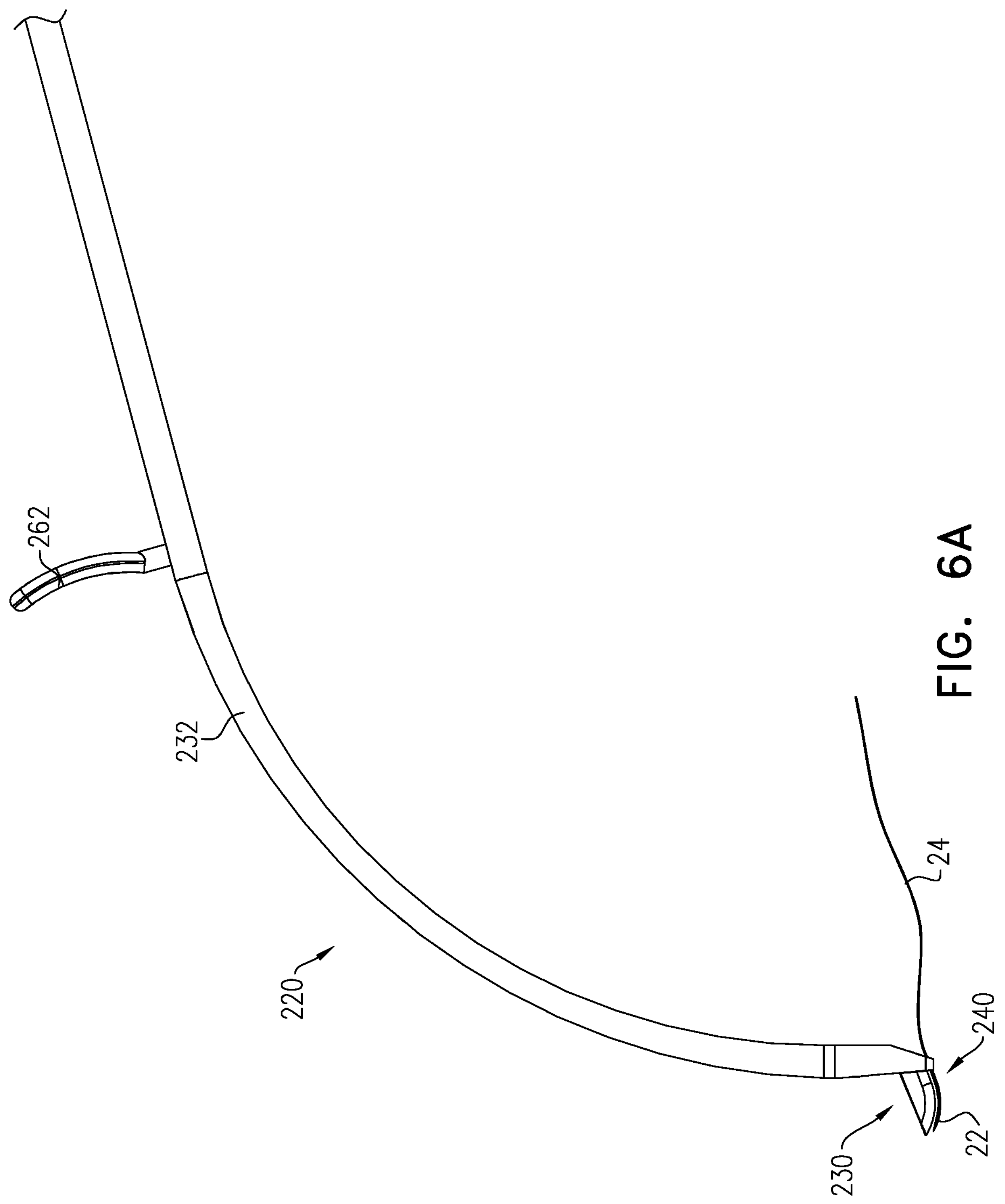
FIGS. 6A-D are schematic illustrations of the needle assembly of FIGS. 5A-D in a non-grasping state, in accordance with an application of the present invention.
Figure 6B:
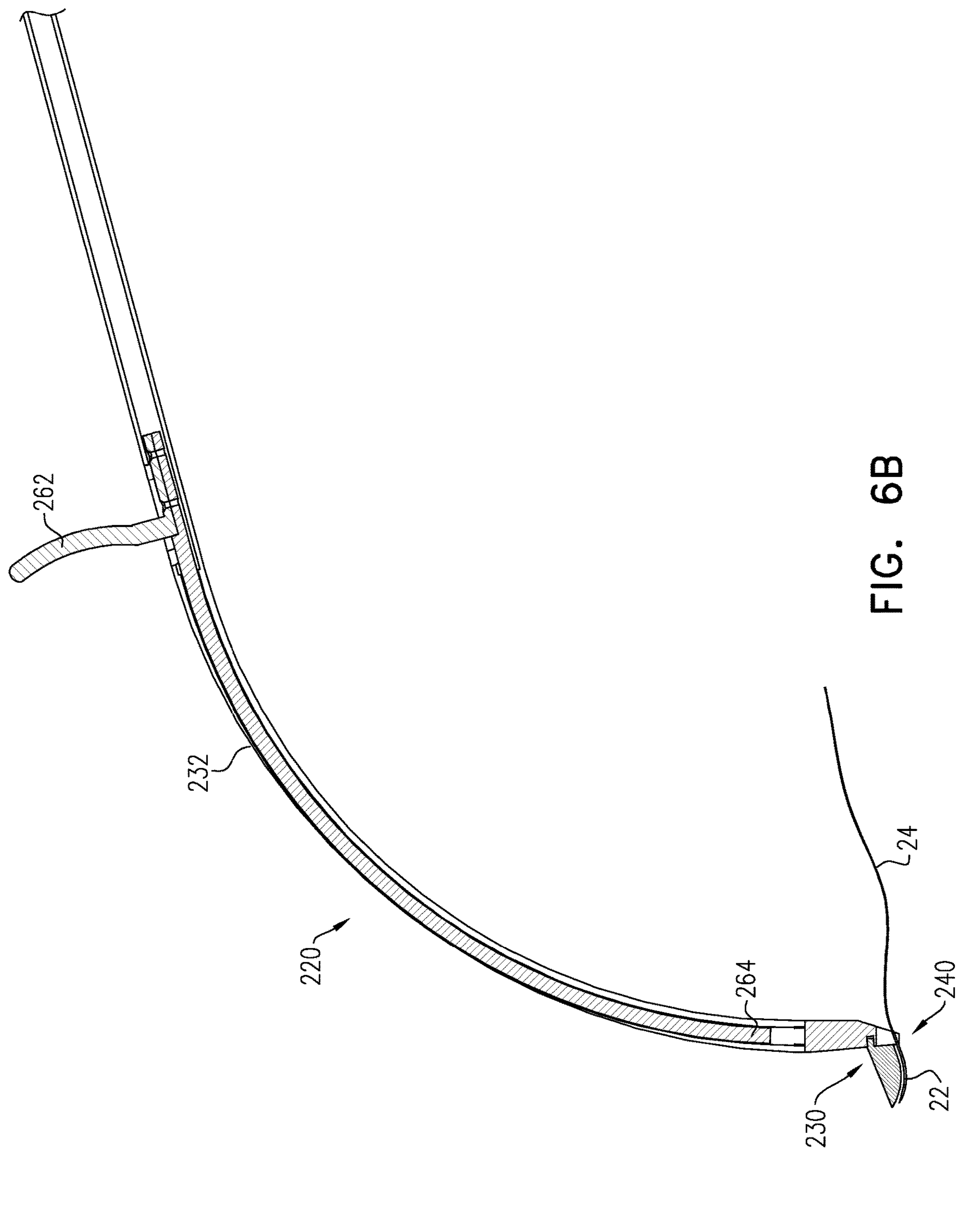
Figure 6C:
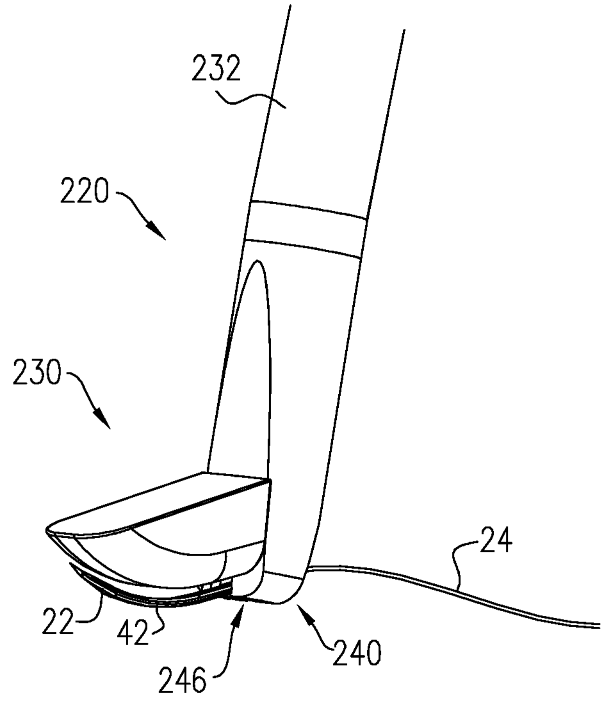
Figure 6D:
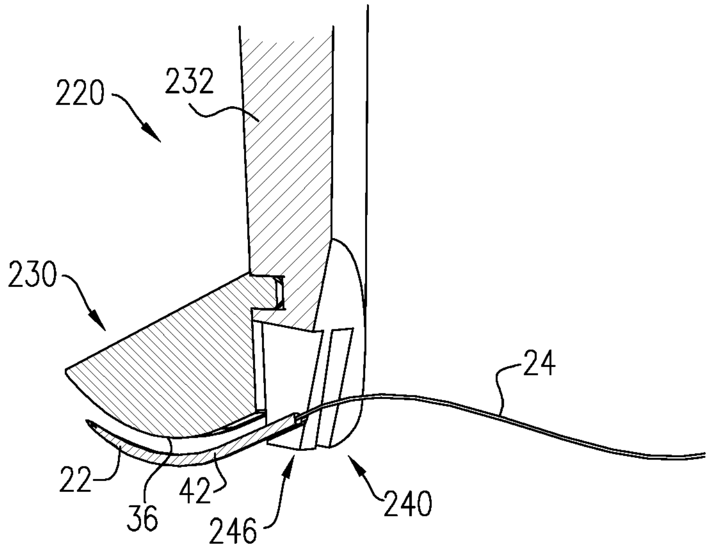

Thereafter, as shown in FIG. 4F, needle 22 is distally pulled, so as to (a) pull suture 24 into tissue 70 at proximal site 76, within tissue 70, and out of tissue 70 at distal site 78 (along the same path through tissue 70 along which needle 22 travels), and (b) pull needle 22 out of tissue 70 at distal site 78. For example, needle 22 may be distally pulled using conventional forceps 88. In this configuration, needle guide tool 30 is typically entirely disengaged from needle 22 before the needle is pulled out of tissue 70.

Alternatively, for applications in which needle guide tool 30 comprises distal needle holder 368, such as described hereinbelow with reference to FIGS. 7A-B and 8A-B, needle 22 may be distally pulled using distal needle holder 368. In this configuration, needle guide tool 30 remains engaged to needle 22 as the needle is pulled out of tissue 70.

As described hereinabove with reference to FIGS. 1A-I, for some applications, needle guide 34, at distal end portion 38 thereof distal to needle-guide surface 36, is shaped so as to define curved surface 39 that faces partially in a distal direction and partially toward body-portion surface 74 when needle-guide surface 36 slidably contacts body-portion surface 74. Curved surface 39 aids with the initial penetration of distal needle tip 56 through body-portion surface 74 at proximal site 76, as shown in FIGS. 4B-C, by tilting needle 22 slightly forward with respect to body-portion surface 74. As soon as needle guide 34 is distally slid slightly along body-portion surface 74, needle-guide surface 36 comes in contact with body-portion surface 74, orienting needle 22 parallel with needle-guide surface and body-portion surface 74, and curved surface 39 tilts away from body-portion surface 74, such that curved surface 39 no longer comes in contact with body-portion surface 74 during the remainder of the procedure.

As described hereinabove with reference to FIGS. 1A-I, proximal needle holder 40 is configured to releasably hold needle 22 by directly contacting longitudinal portion 55 of needle 22, without directly contacting any other portions of needle 22. Typically, sliding needle-guide surface 36 distally along body-portion surface 74 comprises sliding needle-guide surface 36, while needle 22 is entirely exposed except along longitudinal portion 55 of needle 22, distally along body-portion surface 36 such that distal needle tip 56 penetrates body-portion surface 74 at proximal site 76, passes within tissue 70 beneath body-portion surface 74 at the depth no more than the non-zero distance D. and exits body-portion surface 74 at distal site 78 (the precise definition of this depth is provided hereinabove with reference to FIGS. 4C-D).

Typically, the method does not comprise disposing any portions of needle 22 in any passages defined by needle guide tool 30 when needle 22 is held by proximal needle holder 40.

Typically, the method does not comprise sliding any portions of needle 22 through any passages defined by needle guide tool 30 when needle 22 is held by proximal needle holder 40.

Typically, the method does not comprise passing any portions of needle 22 or suture 24 through any passages defined by needle guide tool 30 when needle 22 is held by proximal needle holder 40.

Reference is now made to FIGS. 5A-D and 6A-D, which are schematic illustrations of a needle assembly 220 in a grasping state and a non-grasping state, respectively, in accordance with an application of the present invention. FIGS. 5B, 5D, 6B, and 6D are cross-sectional views. Except as described below, needle assembly 220 is similar to needle assembly 20, described hereinabove with reference to FIGS.

1A-I, and may implement any of the techniques described with reference thereto and/or with reference to needle assembly 120, mutatis mutandis. Although needle assembly 220 is shown as comprising curved needle 22 and longitudinal segment 42 and correspondingly curved needle-guide surface 36, needle assembly 220 may alternatively comprise straight needle 122 and longitudinal segment 142 and correspondingly straight needle-guide surface 136, as described hereinabove with reference to FIG. 2.

A proximal needle holder of a needle guide tool 230 of needle assembly 220 comprises a proximal needle grasper 240, which is configured to assume grasping and non-grasping states. Proximal needle grasper 240 is configured:

- to grasp needle 22 when in the grasping state, such as shown in FIGS. 5A-D, and
- to not grasp needle 22, thereby releasing the needle, when in the non-grasping state, such as shown in FIGS. 6A-D.

For some applications, at the step of the method described hereinabove with reference to FIG. 4F, needle 22 is released from proximal needle grasper 240 by transitioning proximal needle grasper 240 from the grasping state to the non-grasping state.

For some applications, proximal needle grasper 240 is shaped so as to define a slot 246 in which needle 22 is grasped. For some applications, proximal needle grasper 240 further comprises a depressor 248, which is configured to apply grasping pressure to needle 22 when proximal needle grasper 240 is in the grasping state. For example, depressor 248 may indirectly apply the grasping pressure to needle 22, such as by pressing on a wall of slot 246 (such as shown), or may directly apply the grasping pressure to needle 22 (configuration not shown).

For some applications, needle assembly 220 (e.g., a handle 232 thereof) comprises a user control 262 (such as a button, switch, or knob), which is configured to transition proximal needle grasper 240 between the grasping state and the non-grasping state. For example, needle assembly 220 may comprise a shaft 264 that connects (typically mechanically) user control 262 to depressor 248 or another element that causes the grasping of needle 22, and user control 262 is configured to move shaft 264, which in turn moves depressor 248 or the other element that causes the grasping of needle 22. For example, the motion may be axial motion (such as shown) (such as withdrawing depressor 248), rotational motion (not shown), or some other form of motion (not shown).

Reference is now made to FIGS. 7A-B and 8A-B, which are schematic illustrations of a needle assembly 320 with a proximal needle grasper 340 thereof in a grasping state and a non-grasping state, respectively, in accordance with an application of the present invention. Except as described below, needle assembly 320 is similar to needle assembly 120, described hereinabove with reference to FIG. 2, and may implement any of the techniques described with reference thereto and/or with reference to needle assembly 20, mutatis mutandis. Although needle assembly 320 is shown as comprising straight needle 122 and longitudinal segment 142 and correspondingly straight needle-guide surface 136, as described hereinabove with reference to FIG. 2, needle assembly 320 may alternatively comprise curved needle 22 and longitudinal segment 42 and correspondingly curved needle-guide surface 36, as described hereinabove with reference to FIGS. 1A-I.

Figure 7B:
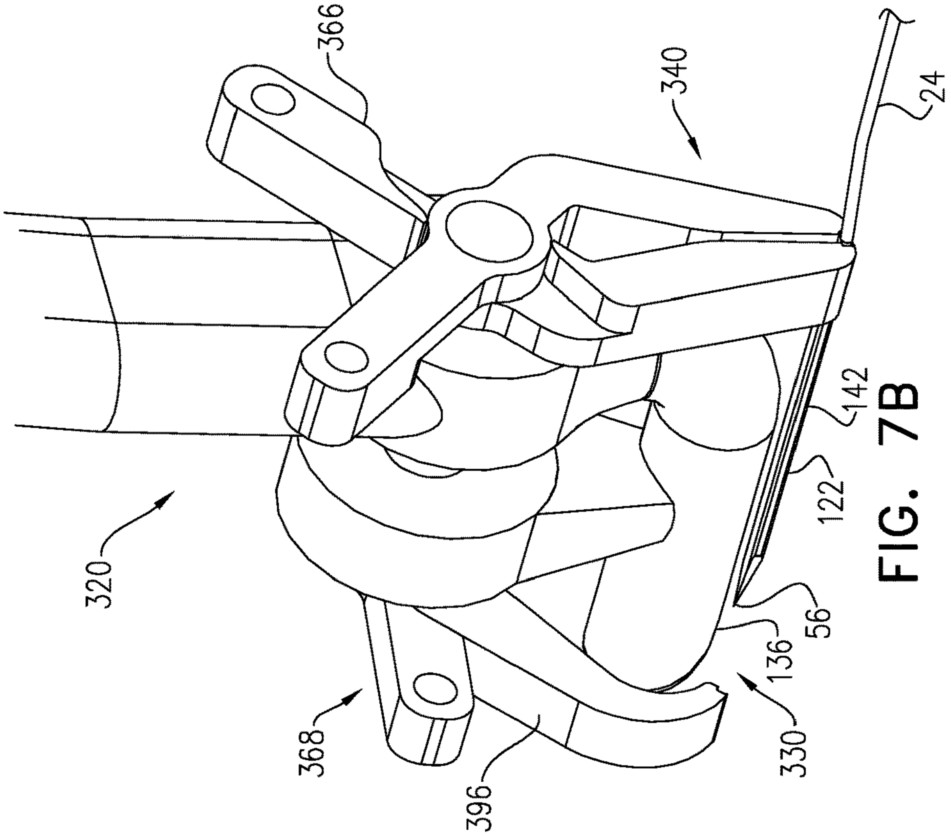
FIGS. 7A-B are schematic illustrations of still another needle assembly with a proximal needle grasper thereof in a grasping state, in accordance with an application of the present invention.
Figure 7A:
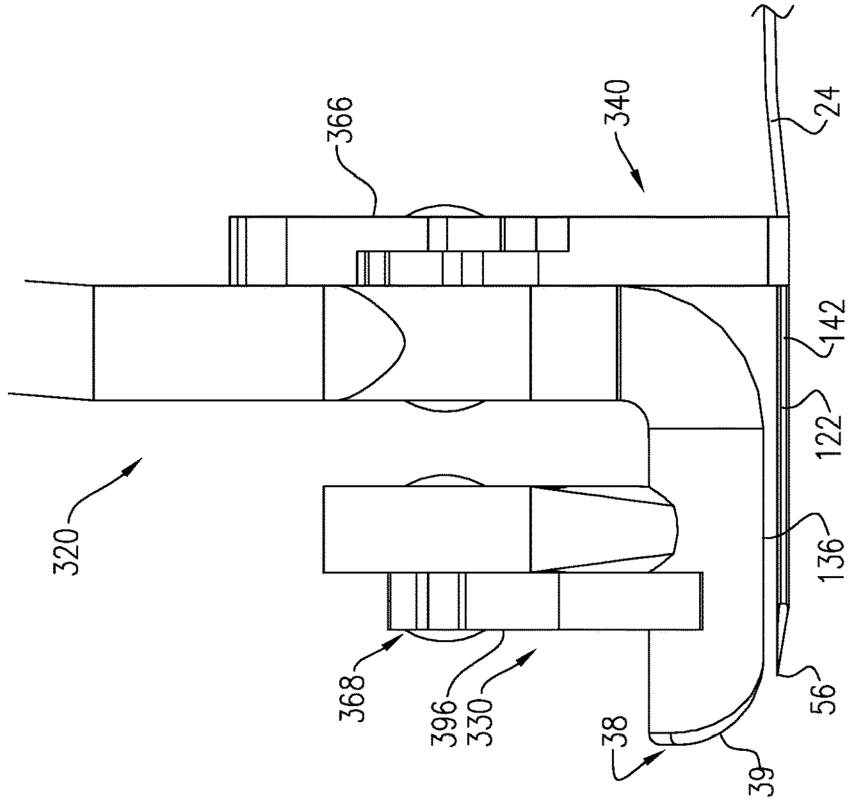
Figure 8B:
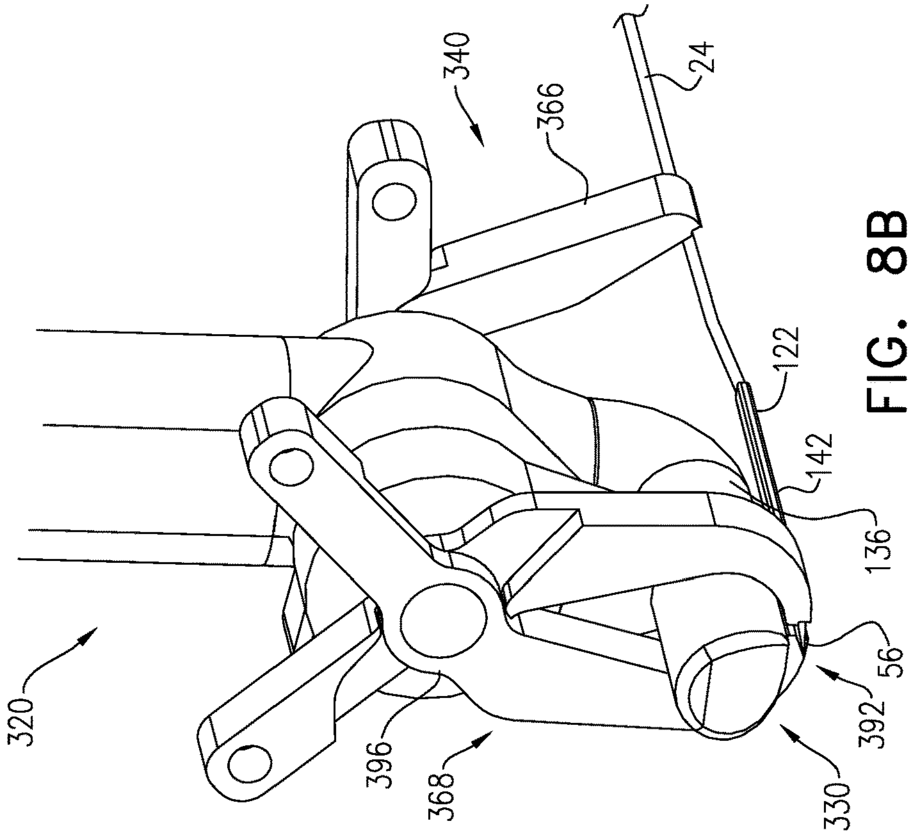
FIGS. 8A-B are schematic illustrations of the needle assembly of FIGS. 7A-B with the proximal needle grasper thereof in a non-grasping state, in accordance with an application of the present invention.
Figure 8A:
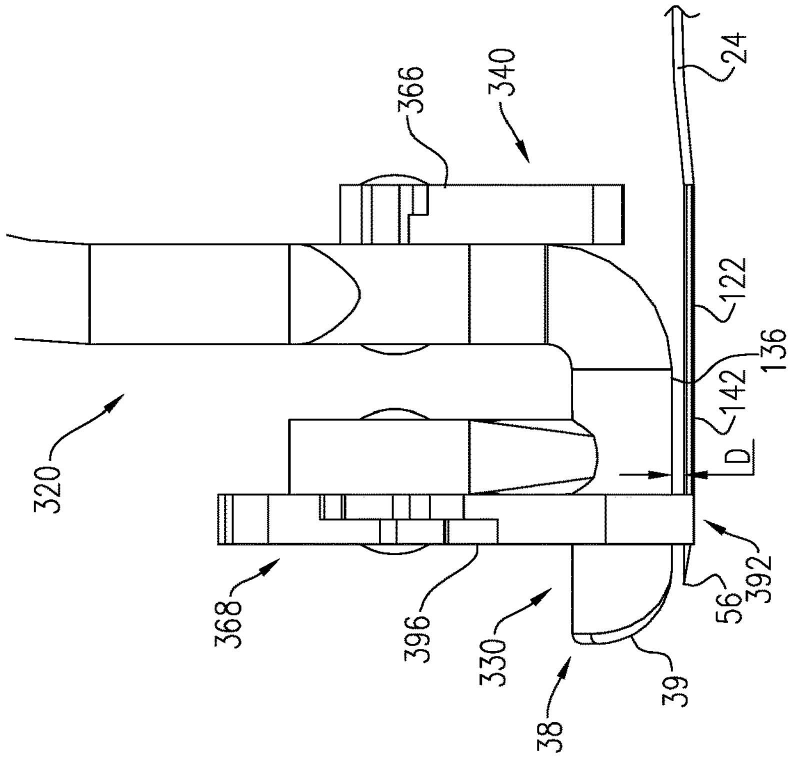

A needle guide tool 330 of needle assembly 320 comprises a needle guide 334 and a proximal needle holder that comprises proximal needle grasper 340, which is configured to assume grasping and non-grasping states, and which comprises forceps 366. Proximal needle grasper 340 is configured:

- to grasp needle 122 when in the grasping state (which might also be considered a closed state), such as shown in FIGS. 7A-B, and
- to not grasp needle 122, thereby releasing the needle, when in the non-grasping state (which might also be considered an open state), such as shown in FIGS. 8A-B.

For some applications, at the step of the method described hereinabove with reference to FIG. 4F, needle 122 is released from proximal needle grasper 340 by transitioning proximal needle grasper 340 from the grasping state to the non-grasping state.

For some applications, needle guide tool 330 further comprises a distal needle holder 368, which is configured to hold a distal portion 392 of needle 122. The other needle guide tools described herein may optionally comprise needle guide tool 330, mutatis mutandis.

For some applications, distal needle holder 368 is configured to hold distal portion 392 of needle 122 such that longitudinal segment 142 of needle 122 runs alongside needle-guide surface 136 at the non-zero distance D therefrom that does not vary along longitudinal segment 142 of needle 122, even when the proximal needle holder (e.g., proximal needle grasper 340) is not holding needle 122. This allows the safe, controlled pulling of needle 122 within tissue 70 and out of tissue 70 at distal site 78, without the risk of applying a lateral force to the needle such as might occur if the needle were grasped with conventional forceps separately from needle guide tool 330.

For some applications, distal needle holder 368 is configured to hold needle 122 such that needle 122 is fixed with respect to needle guide 334 (but not necessarily longitudinally or rotationally fixed with respect to needle guide 334).

Typically, distal needle holder 368 is configured to hold needle 122 such that needle 122 is longitudinally fixed with respect to needle guide 334 (but not necessarily rotationally fixed with respect to needle guide 334).

A closest distance between the proximal and the distal needle holders depends on the length of needle 122, and may be, for example, between 5 and 12 mm.

For some applications, at the step of the method described hereinabove with reference to FIG. 4G, needle 122 is distally pulled out of tissue 70 at distal site 78 comprises:

- holding, with distal needle holder 368, distal portion 392 of needle 122 that exited body-portion surface 74 at distal site 78; and
- while holding distal portion 392 of needle 122 with distal needle holder 368, sliding needle-guide surface 136 along body-portion surface 74 such that distal needle holder 368 pulls needle 122 out of tissue 70 at distal site 78.

For some applications, distal needle holder 368 is configured to hold distal portion 392 of needle 122 such that longitudinal segment 42 of needle 122 runs alongside needle-guide surface 136 at the non-zero distance D therefrom that does not vary along longitudinal segment 42 of needle 122, even when proximal needle holder 40 is not holding needle 122.

For some applications, distal needle holder 368 comprises a distal needle grasper 394, which is configured to assume grasping and non-grasping states, and which is configured, when in the grasping state, to grasp distal portion 392 of needle 122. For some applications, distal needle grasper 394 comprises forceps 396, as shown in FIGS. 7A-B and 8A-B.

Typically, proximal and distal needle graspers 340 and 394 are independently transitionable between their respective non-grasping and grasping states.

For some applications, at the step of the method described hereinabove with reference to FIG. 4G, distal portion 392 of needle 122 is grasped with distal needle grasper 394 by transitioning distal needle grasper 394 from the non-grasping state to the grasping state. For some applications, transitioning proximal needle grasper 340 to the non-grasping state and transitioning distal needle grasper 394 to the grasping state comprise transitioning proximal needle grasper 340 to the non-grasping state independently of transitioning distal needle grasper 394 to the grasping state.

Reference is made to FIGS. 1A-8B. For some applications, any of the configurations of needle guide tool 30, 130, 230, 330 described herein may optionally be modified as follows. Handle 32, 232 and needle guide 34, 134, 334 are discrete elements that are not integral or permanently coupled to each other. Instead, handle 32, 232 is configured to be removably coupled to needle guide 34, 134, 334, such as by a healthcare worker during or soon before a procedure performed using the needle guide tool. Typically, the handle, by grabbing the needle guide, stabilizes the needle to the needle guide, such as providing additional pressure at the site where the needle is coupled to the needle guide.

Typically, needle guide tool 30, 130, 230, 330 is provided with needle 22 already coupled to (preloaded on) proximal needle holder 40 of needle guide 34, 134, 334. Optionally, the handle is configured to be activated (e.g., by user control 262) to disengage needle 22 from the proximal needle holder. Optionally, handle 32, 232 is decoupled from needle guide 34, 134, 334 after the procedure.

Alternatively, the needle guide tool is configured such that removal of the handle from the needle guide automatically releases the needle from the needle guide, leaving the needle in the tissue to be passed with the suture.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for passing, through tissue of a portion of an eye of a subject, a needle and a suture coupled to the needle, the method comprising:

positioning a needle guide of a needle guide tool such that a needle-guide surface of the needle guide contacts a body-portion surface of the portion of an eye, while a proximal needle holder of the needle guide tool releasably holds the needle such that a longitudinal segment of the needle runs alongside the needle-guide surface at a non-zero distance therefrom that does not vary along the longitudinal segment of the needle;

sliding the needle-guide surface distally along the body-portion surface such that a distal needle tip (a) penetrates the body-portion surface at a proximal site, (b) passes within the tissue beneath the body-portion surface at a depth no more than the non-zero distance, the depth measured between the body-portion surface and an edge of the needle closest to the body-portion surface, and (c) exits the body-portion surface at a distal site distal to the proximal site, while the needle guide and the needle held by the proximal needle holder remain outside the portion of an eye, and while the needle-guide surface slides along the body-portion surface;

thereafter, releasing the needle from the proximal needle holder; and thereafter, distally pulling the needle, so as to (a) pull the suture into the tissue at the proximal site, within the tissue, and out of the tissue at the distal site, and (b) pull the needle out of the tissue at the distal site.

2. The method according to claim 1, wherein the needle is straight.

3. The method according to claim 1, wherein the needle is curved.

4. The method according to claim 1, wherein the needle guide tool further comprises a handle, which supports the needle guide.

5. The method according to claim 1, wherein a length of the needle-guide surface is between 40% and 120% of a length of the needle.

6. The method according to claim 1, wherein the longitudinal segment of the needle includes an entirety of the needle that runs alongside the needle-guide surface.

7. The method according to claim 1, wherein the needle-guide surface is straight along a longitudinal axis thereof parallel to the needle when the needle is held by the proximal needle holder.

8. The method according to claim 1, wherein the needle-guide surface is convexly curved along a longitudinal axis thereof parallel to the needle when the needle is held by the proximal needle holder.

9. The method according to claim 1, wherein a lower surface of the needle guide is shaped so as to define (a) the needle-guide surface and (b) a window that passes through the needle guide from an upper surface of the needle guide to the lower surface of the needle guide, and wherein the method further comprises viewing of a portion of the needle through the window.

10. The method according to claim 1, wherein the needle guide tool is not shaped so as to define any passages in which any portion of the needle is disposed when the needle is held by the proximal needle holder.

11. The method according to claim 1, wherein the non-zero distance is less than a thickness of the tissue within which the distal needle tip passes.

12. The method according to claim 1, wherein sliding the needle-guide surface along the body-portion surface comprises sliding the needle-guide surface along the body-portion surface while the proximal needle holder holds the needle such that the needle is longitudinally fixed with respect to the needle guide.

13. The method according to claim 1, wherein the proximal needle holder releasably holds the needle by directly contacting a longitudinal portion of the needle, without directly contacting any other portions of the needle, and wherein sliding the needle-guide surface distally along the body-portion surface comprises sliding the needle-guide surface, while the needle is entirely exposed except along the longitudinal portion of the needle, distally along the body-portion surface such that the distal needle tip penetrates the body-portion surface at the proximal site, passes within the tissue beneath the body-portion surface at the depth no more than the non-zero distance, and exits the body-portion surface at the distal site.

14. The method according to claim 1, wherein the tissue includes a sclera of the eye, and wherein sliding the needle-guide surface along the body-portion surface of the portion of the eye comprises sliding the needle-guide surface along the body-portion surface of the portion of the eye such that the distal needle tip penetrates the body-portion surface of the portion of the eye at the proximal site, passes within the sclera of the eye beneath the body-portion surface at the depth no more than the non-zero distance, and exits the body-portion surface of the portion of the eye at the distal site.

* * * * *